US012642912B2

(12) United States Patent
Cha et al.

(10) Patent No.: US 12,642,912 B2
(45) Date of Patent: Jun. 2, 2026

(54) SYSTEMS AND METHODS FOR PRE-FILLED MEDICAL DELIVERY ASSEMBLIES

(71) Applicant: Koska Family Limited, East Sussex (GB)

(72) Inventors: Jae-Hyok Cha, Gongju-si (KR); Hanjin In, Toronto (CA); Marc Andrew Koska, East Sussex (GB); Jeff Price, Windermere, FL (US)

(73) Assignee: ApiJect, Stamford, CT (US)

( * ) Notice: Subject to any disclaimer, the term of this patent is extended or adjusted under 35 U.S.C. 154(b) by 527 days.

(21) Appl. No.: 18/006,972

(22) PCT Filed: Jul. 21, 2021

(86) PCT No.: PCT/US2021/042671
§ 371 (c)(1),
(2) Date: Jan. 26, 2023

(87) PCT Pub. No.: WO2022/026275
PCT Pub. Date: Feb. 3, 2022

(65) Prior Publication Data
US 2023/0270951 A1 Aug. 31, 2023

Related U.S. Application Data

(60) Provisional application No. 63/058,684, filed on Jul. 30, 2020.

(51) Int. Cl.
*A61M 5/32* (2006.01)

(52) U.S. Cl.
CPC ....... *A61M 5/32* (2013.01); *A61M 2005/3217* (2013.01)

(58) Field of Classification Search
CPC ..................... A61M 5/32; A61M 2005/3217
See application file for complete search history.

(56) References Cited

U.S. PATENT DOCUMENTS 6,053,892 A 4/2000 Meyer
8,486,501 B2 7/2013 Manabe
10,363,369 B2 7/2019 Cosman
(Continued)

FOREIGN PATENT DOCUMENTS

CN 102869399 1/2013
DE 202018107232 2/2019
(Continued)

OTHER PUBLICATIONS

Extended European Search Report (EESR) for European Patent Application 21783754.1 dated Jun. 25, 2024; 9 pps.
(Continued)

*Primary Examiner* — Dung T Ulsh
(74) *Attorney, Agent, or Firm* — RowanTree Law Group, PLLC; Carson C.K. Fincham

(57) ABSTRACT
A pre-filled medical delivery assembly assembled and configured to allow delivery of a single dose of a therapeutic agent (e.g., vaccine, drug, medicament, etc.) from a Blow-Fill-Seal (BFS) vial to a patient. The delivery assembly generally includes a modular design consisting of separately constructed components cooperatively arranged and coupled to one another.

11 Claims, 10 Drawing Sheets

(56) References Cited

U.S. PATENT DOCUMENTS

| | | | |
|---|---|---|---|
| 2005/0049560 | A1 | 3/2005 | Hauri |
| 2006/0276759 | A1 | 12/2006 | Kinast |
| 2009/0171311 | A1 | 7/2009 | Genosar |
| 2013/0144218 | A1 | 6/2013 | Daniel |
| 2014/0046270 | A1 | 2/2014 | Thornton |
| 2014/0323975 | A1 | 10/2014 | Thornton |
| 2015/0136622 | A1 | 5/2015 | Genosar |
| 2015/0283332 | A1* | 10/2015 | Woehr .................. A61M 5/002 221/26 |
| 2015/0313525 | A1 | 11/2015 | Ebetsberger |
| 2017/0143912 | A1* | 5/2017 | Hu ...................... A61M 5/3202 |
| 2017/0189270 | A1* | 7/2017 | Nazzaro .............. A61M 5/1782 |
| 2018/0085527 | A1 | 3/2018 | Taylor |
| 2019/0060168 | A1 | 2/2019 | Koska |
| 2019/0217019 | A1* | 7/2019 | Kondo .................... A61M 5/28 |
| 2021/0128835 | A1 | 5/2021 | Koska |

FOREIGN PATENT DOCUMENTS

| | | | |
|---|---|---|---|
| RU | 2643432 | | 2/2018 |
| WO | 2004075955 | A1 | 9/2004 |
| WO | 2017001925 | | 1/2017 |
| WO | 2019038751 | | 2/2019 |
| WO | 2019219480 | | 11/2019 |
| WO | 2019246435 | | 12/2019 |
| WO | 2021207040 | | 10/2021 |
| WO | 2022026275 | | 2/2022 |
| WO | 2022120269 | | 6/2022 |
| WO | 2023018840 | | 2/2023 |

OTHER PUBLICATIONS

Extended European Search Report (EESR) for European Patent Application No. 21901603.7 mailed on Sep. 13, 2024 (10 pages).
Extended European Search Report for European Patent Application No. EP21850313 mailed Jul. 29, 2024; 8 pgs.
Intention to Grant (Notice of Allowance) for European Patent Application No. EP22762208.1 mailed Jun. 14, 2024; 35 pgs.
International Search Report for Application PCT/US2021/025683 dated Jul. 8, 2021; 2 pps.
International Search Report for Application PCT/US21/042671 dated Nov. 5, 2021; 2 pps.
International Search Report for Application PCT/US22/40006 dated Nov. 7, 2022; 5 pps.
International Search Report for PCT Application No. PCT/US21/61991 dated Feb. 16, 2022; 2 pps.
International Written Opinion for PCT Application No. PCT/US21/61991 dated Feb. 16, 2022; 9 pps
Written Opinion for Application PCT/US2021/025683 dated Jul. 8, 2021; 4 pps.
Written Opinion for Application PCT/US21/042671 dated Nov. 5, 2021; 9 pps.
Written Opinion for PCT/US22/40006 dated Nov. 7, 2022; 6 pps.
European Examination Report (Office Action) for European Patent Application 21783754.1 dated May 20, 2025; 6 pgs.
First Office Action for Chinese Patent Application No. 202180052645.8 mailed on May 23, 2025; 4 pgs.
Office Action for Chinese Patent Application No. 202180027126.6 mailed on May 28, 2025 (6 pages).
Office Action for Chinese Patent Application No. 202180027126.6 mailed on Nov. 1, 2025 (5 pages).
Office Action for Indian Patent Application No. 202227056739 mailed on Oct. 29, 2025 (6 pages).
Notice of Allowance/Intention to Grant for Chinese Patent Application No. 202180052645.8 mailed on Nov. 26, 2025; 1 pg.

* cited by examiner

SYSTEMS AND METHODS FOR PRE-FILLED MEDICAL DELIVERY ASSEMBLIES

CROSS-REFERENCE TO RELATED APPLICATIONS

Benefit and priority is claimed to, and this is a National Stage pursuant to 35 U.S.C. § 371 of, International Patent Application PCT/US21/042671 filed on Jul. 21, 2021 and titled "SYSTEMS AND METHODS FOR PRE-FILLED MEDICAL DELIVERY ASSEMBLIES", which itself claims benefit and priority under 35 U.S.C. § 119(e) to, and is a Non-provisional of, U.S. Provisional Patent Application No. 63/058,684 filed on Jul. 30, 2020 and titled "PRE-FILLED MEDICAL DELIVERY ASSEMBLIES", which is hereby incorporated by reference herein in its entirety.

BACKGROUND

Every year, millions of people become infected and die from a variety of diseases, some of which are vaccine-preventable. Although vaccination has led to a dramatic decline in the number of cases of several infectious diseases, some of these diseases remain quite common. In many instances, large populations of the world, particularly in developing countries, suffer from the spread of vaccine-preventable diseases due to ineffective immunization programs, either because of poor implementation, lack of affordable vaccines, or inadequate devices for administering vaccines, or combinations thereof.

Some implementations of immunization programs generally include administration of vaccines via a typical reusable syringe. However, in many situations, particularly in developing countries, the administration of vaccines occur outside of a hospital and may be provided by a non-professional, such that injections are given to patients without carefully controlling access to syringes. The use of reusable syringes under those circumstances increases the risk of infection and spread of blood-borne diseases, particularly when syringes, which have been previously used and are no longer sterile, are used to administer subsequent injections. For example, the World Health Organization (WHO) estimates that blood-borne diseases, such as Hepatitis and human immunodeficiency virus (HIV), are being transmitted due to reuse of such syringes, resulting the death of more than one million people each year.

Previous attempts at providing single-use or disposable injection devices to remedy such problems in the industry have achieved measurable success but have failed to adequately remedy the existing problems. Pre-filled, single-use injection devices manufactured via injection molding or Form-Fill-Seal (FFS) processes, such as the Uniject™ device available from the Becton, Dickinson and Company of Franklin Lakes, NJ, for example, while offering precise manufacturing tolerances in the range of two thousandths of an inch (0.002-in; 50.8 μm) to four thousandths of an inch (0.004-in; 101.6 μm)—for hole diameters in molded parts, require separate sterilization processes (e.g., gamma radiation) that are not compatible with certain fluids, provide production rates limited to approximately nine thousand (9,000) non-sterile units per hour, and can be provided to an end-user for approximately one dollar and forty cents ($1.40) per dose/unit.

BRIEF DESCRIPTION OF THE DRAWINGS

An understanding of embodiments described herein and many of the attendant advantages thereof may be readily obtained by reference to the following detailed description when considered with the accompanying drawings, wherein.

DETAILED DESCRIPTION

I. Introduction

Figures 1A, 1B, 1C:
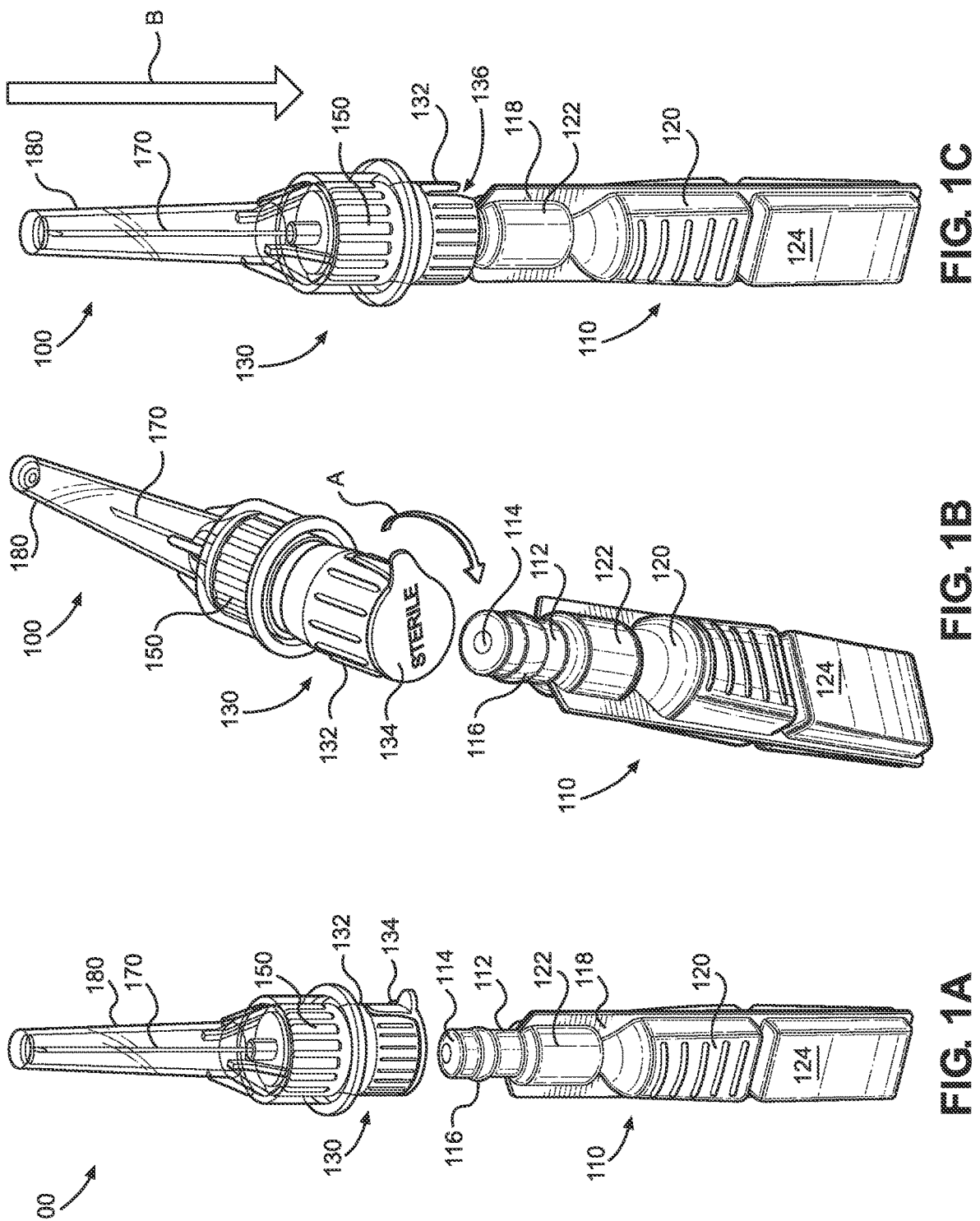
FIG. 1A, FIG. 1B, FIG. 1C, FIG. 1D, FIG. 1E, and FIG. 1F are various views of a pre-filled medical delivery assembly according to some embodiments.

Embodiments of the present invention provide systems and methods for pre-filled medical delivery assemblies that overcome drawbacks of current delivery devices and methods. For example, the pre-filled medical delivery assemblies of some embodiments may include a Blow-Fill-Seal (BFS) vial or bottle coupled to a specialized collar that facilitates coupling of an administration member (e.g., a needle) to the BFS vial. In some embodiments, such a pre-filled medical delivery assembly may be selectively actuated by application of rotational force to a cap covering the administration member, causing the administration member to axially advance and pierce a fluid reservoir of the BFS vial. Utilization of such systems that employ BFS vials may be advantageous and may address various shortcomings of previous systems.

BFS vials may, for example, offer a less expensive alternative to typical vials or devices created via other manufacturing techniques. In some embodiments, BFS vials (e.g., due to the nature of the BFS manufacturing process) may not require separate sterilization (e.g., an may accordingly be compatible with a wider array of fluids), may provide enhanced production rates of sterile/aseptic units per hour, and/or may be provided to an end-user for significantly lower per dose/unit costs. In some embodiments, these advantages may come with an attendant drawbacks of reduced manufacturing tolerances and other disadvantages of utilizing a "soft" plastic (e.g., having a Shore/Durometer "D" hardness of between 60 and 70). BFS processes may, for example, offer less precise manufacturing tolerances in the range of five hundredths of an inch (0.05-in; 1.27 mm) to fifteen hundredths of an inch (0.15-in; 3.81 mm)—for linear dimensions, e.g., in accordance with the standard ISO 2768-1 "General tolerances for linear and angular dimensions without individual tolerance indications" published by the International Organization for Standardization (ISO) of Geneva, Switzerland (Nov. 15, 1989) and/or may not be readily adaptable to form certain mating features such as standardized threads. In some embodiments, these drawbacks and/or the deficiencies of prior systems may be advantageously addressed by specific features, configurations, and/or components as described hereinafter.

II. Pre-filled Medical Delivery Assemblies—Exterior threaded Coupling

Referring initially to FIG. 1A, FIG. 1B, FIG. 1C, FIG. 1D, FIG. 1E, and FIG. 1F, various views of a pre-filled medical delivery assembly 100 according to some embodiments are shown. In some embodiments, the pre-filled medical delivery assembly 100 may comprise various inter-connected and/or modular components such as a BFS vial 110 comprising and/or defining a vial neck 112, a fluid seal 114, a mounting flange 116, a bottle flange 118, a collapsible reservoir 120, a dispensing reservoir 122, and/or an identification area 124. According to some embodiments, the pre-filled medical delivery assembly 100 may comprise an administration (e.g., injection) module or component 130 that is manufactured, assembled, and/or provided as a separate unit from the BFS vial 110. In some embodiments, the administration component 130 may comprise a mounting collar 132 which itself comprises, is coupled to, and/or defines various features and/or elements. The mounting collar 132 and/or the administration assembly 130 may, for example, be maintained as a closed and/or sterile component via a seal 134 (e.g., a foil, wax, paper, and/or other thin, pierceable, tear-able, and/or removable object or layer coupled to the mounting collar 132 and/or the administration component 130) that seals an interior volume or socket (not separately labeled) of the mounting collar 132, disposed at a first end thereof. According to some embodiments, the mounting collar 132 may comprise one or more coupling or mounting features 136, an internal seat 138 (e.g., that is configured to accept the mounting flange 116 of the BFS vial 110 in the case that the neck 112 of the BFS vial 110 is inserted into the mounting collar 132 and/or the administration component 130), a puncture seal 140, and/or external threads 142). In some embodiments, the mounting collar 132 may comprise and/or define an exterior flange 144 (e.g., a radial flange) that is operable to receive, mate with, and/or otherwise engage with a needle hub 150. In some embodiments, the needle hub 150 may couple to the mounting collar 132 via threads 152 thereof that correspond to and/or mate with the threads 142 of the mounting collar 132. According to some embodiments, the needle hub 150 may comprise, couple to and/or house a needle, cannula, and/or other administration member 170, and/or a cap 180 (e.g., selectively engaged and/or coupled to the needle hub 150 to shroud, house, and/or protect the administration member 170). According to some embodiments, the pre-filled medical delivery assembly 100 may include a modular design consisting of separately constructed components 110, 130, 132, 150, 170, 180 cooperatively arranged and coupled to one another.

In some embodiments, the collapsible reservoir 120 may be filled (fully or partially) with a fluid or other agent (not separately shown) to be delivered, e.g., to a patient (not shown). According to some embodiments, the fluid may be injected into the BFS vial 110 in a sterile environment during manufacture via a BFS process and sealed within the BFS vial 110 via the fluid seal 114. The fluid seal 114 may comprise a portion of the molded BFS vial 110 for example that is configured to be pierced to expel the fluid, e.g., such as by providing a flat or planar piercing surface and/or by being oriented normal to an axis of the BFS vial 110 (and/or the pre-filled medical delivery assembly 100). In some embodiments, the fluid seal 114 may comprise a foil, wax, paper, and/or other thin, pierceable object or layer coupled to the BFS vial 110. In some embodiments, the neck 112 of the BFS vial 110 may comprise the mounting flange 116 such as, e.g., the "doughnut"-shaped exterior flange depicted. The mounting flange 116 may, for example, provide a radially elastic mating surface that is operable to provide a selective engagement or fit within the socket of the administration component 130.

According to some embodiments, the fluid may generally pass between the collapsible reservoir 120 and the connected dispensing reservoir 122. In some embodiments, a juncture, valve, and/or passage (not separately labeled) between the dispensing reservoir 122 and the collapsible reservoir 120 may restrict flow such that the fluid may readily enter one of the dispensing reservoir 122 and the collapsible reservoir 120 but may not readily return to the other reservoir 120, 122. Such a constriction may in some embodiments, provided advantages as described herein. In some embodiments, the constriction may not be necessary or desirable, such as in the case that the collapsible reservoir 120 and the dispensing reservoir 122 are formed and/or combined as a single, unobstructed reservoir, e.g., a single fluid reservoir (not shown).

In some embodiments, the pre-filled medical delivery assembly 100 may include a modular design consisting of separately constructed components 110, 130 cooperatively arranged and coupled to one another. As depicted in FIG. 1A, for example, the BFS vial 110 and the administration component 130 may be manufactured, packaged, shipped, stored, and/or provided as separate components. In such a manner, the administration component 130 may not need to be stored or shipped in accordance with often restrictive requirements imposed on medicaments and may accordingly reduce the amount of space required for such specialized storage and/or shipping. The administration component 130 may also or alternatively be manufactured, stored, and/or shipped in advance (e.g., at a first time) while the BFS vial 110 that is pre-filled with the fluid may be manufactured, stored, and/or shipped at a later time (e.g., a second time). In some embodiments, the delay between the first time and the second time may be lengthy without causing detrimental effects, as the administration component 130 may be stored, in some embodiments, indefinitely. In such a manner, units of the administration component 130 may be provided to be on-hand in advance of the availability and/or arrival of the BFS vial 110, reducing supply chain constraints in the case of proactive administration component 130 procurement.

According to some embodiments, the components 110, 130 may be coupled, e.g., in the field and/or in situ, to provide an active pre-filled (e.g., injectable) medical delivery device. As shown in FIG. 1B, for example, the seal 134 may be removed from the administration component 130 (at "A") and the administration component 130 (and/or the socket thereof) may be aligned with the neck 112 of the BFS vial 110. According to some embodiments, the administration component 130 (and/or the mounting collar 132 thereof) may be axially engaged to couple with the BFS vial 110 via application of a mating axial force, as shown in FIG. 1C (at "B"). The administration component 130 (and/or the mounting collar 132 thereof) may be urged onto the neck 112 of the BFS vial 110, for example, such that the cooperatively shaped internal seat 138 (e.g., an interior groove or channel) accepts the mounting flange 116, thereby removably coupling the BFS vial 110 and the administration component 130 (and/or the mounting collar 132 thereof). In some embodiments, the internal seat 138 (and/or other interior features) and/or the mounting flange 116 may be shaped such that uncoupling of the BFS vial 110 and the administration component 130 (and/or the mounting collar 132 thereof) is mechanically prohibited. In some embodiments, the mounting flange 116 may be shaped as an axially elongated rounded exterior flange (e.g., the "doughnut" shape as depicted) and/or the internal seat 138 may comprise a cooperative and/or mirrored axially elongated rounded interior groove or track. According to some embodiments, the one or more mounting features 136 such as the mirrored axial slits depicted may engage with the bottle flange 118 (and/or portions of the BFS vial 110) such that rotation of the administration component 130 (and/or the mounting collar 132 thereof) with respect to the BFS vial 110 is restricted in the case that they are coupled. In some embodiments, the coupling of the BFS vial 110 and the administration component 130 (and/or the mounting collar 132 thereof) may be configured to explicitly permit free rotation (e.g., about a common axis) of the BFS vial 110 with respect to the administration component 130 (and/or the mounting collar 132 thereof). The mounting features 136 may not, in some embodiments for example, engage with the BFS vial 110 (and/or the mounting flange 116 thereof), e.g., to permit rotation therebetween.

Figures 1D, 1E, 1F:
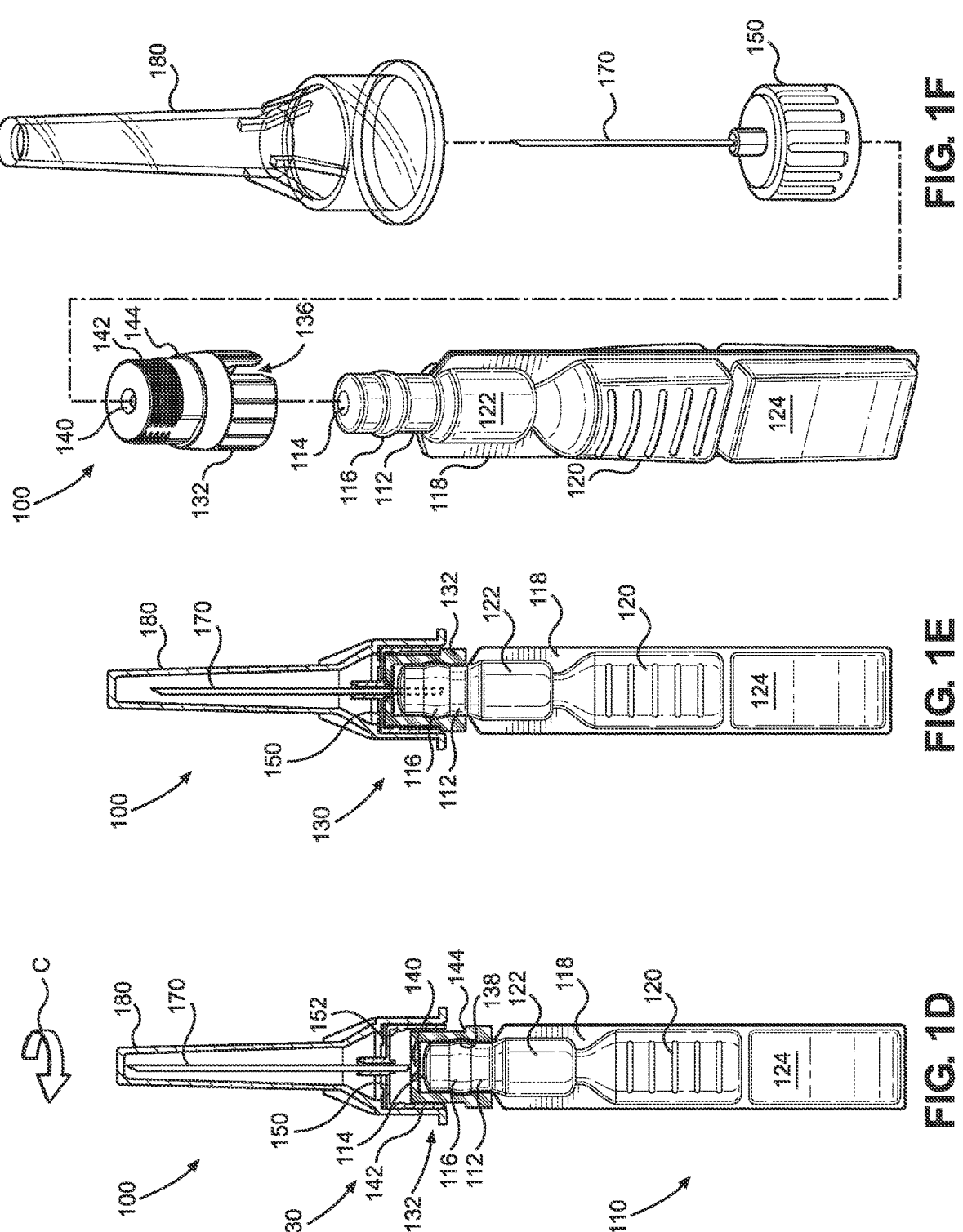
Figures 2A, 2B, 2C, 2D, 2E, 2F, 2G:
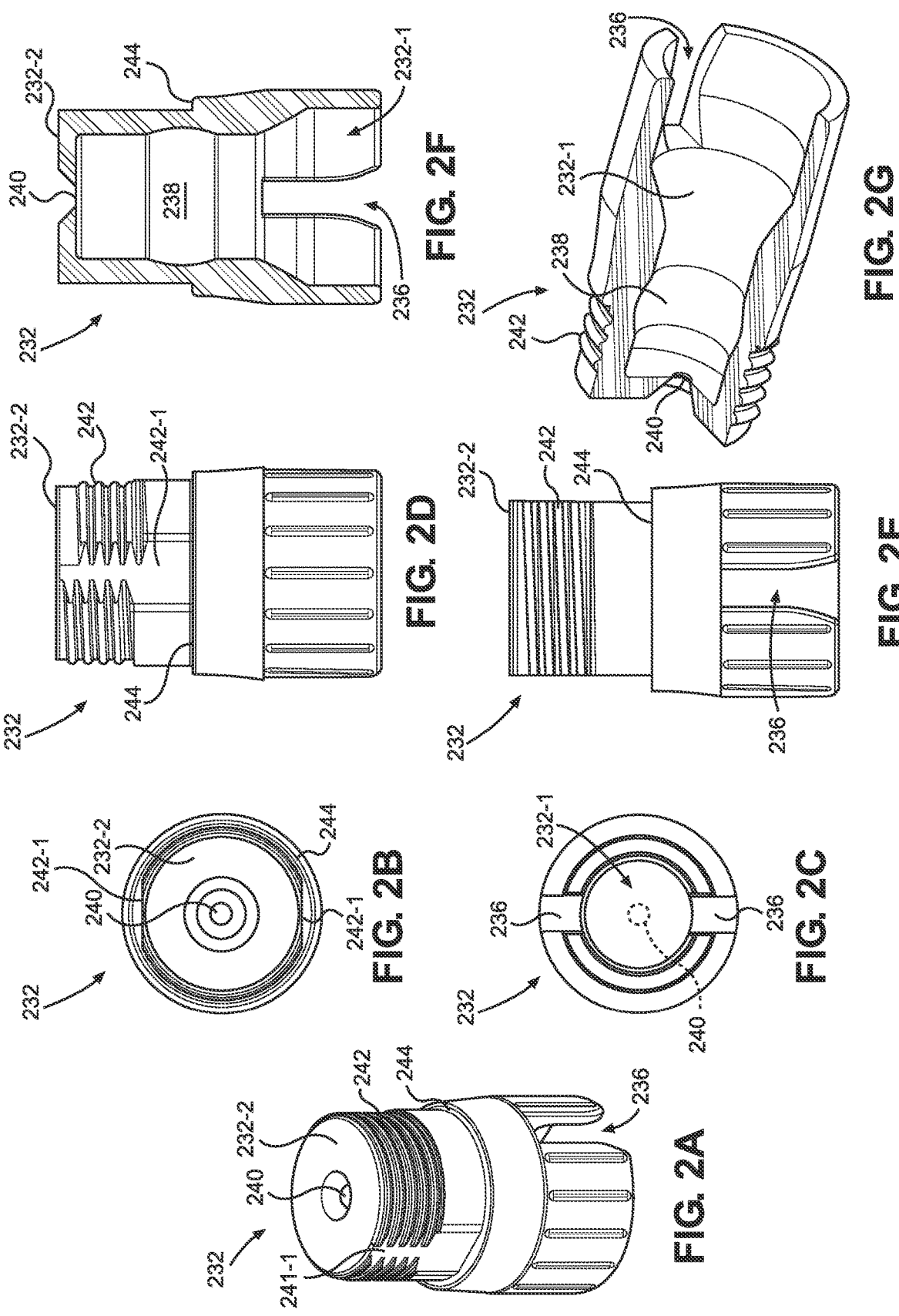
FIG. 2A, FIG. 2B, FIG. 2C, FIG. 2D, FIG. 2E, FIG. 2F, and FIG. 2G are various views of a pre-filled medical delivery assembly coupling according to some embodiments.

As depicted in FIG. 1D, in some embodiments the neck 112 of the BFS vial 110 may be urged and/or forced into the socket of the mounting collar 132 until the mounting flange 116 becomes seated in (and/or coupled to or mated with) the internal seat 138 (e.g., a seated position). In such a manner, the fluid seal 114 may be advantageously positioned adjacent to the puncture seal 140. According to some embodiments, the mounting flange 116 may be configured as the doughnut shape (as depicted) to provide various advantages to the pre-filled medical delivery assembly 100. The axial elongation of the mounting flange 116 may, for example, provide for a smooth, uniform, and/or less forceful mating process that is less likely to deform the soft plastic neck 112 of the BFS vial 110 and/or may provide for a lengthened mating surface that is more likely to prevent leakage of the fluid. In some embodiments, the mounting flange 116 and the cooperatively shaped and sized internal seat 138 may permit simple, effective, and/or economic attachment of the administration component 130 to the BFS vial 110.

In some embodiments, the needle hub 150 may be coupled to the mounting collar 132 via engagement of the external threads 142 of the mounting collar 132 with the internal threads 152 of the needle hub 150. The internal threads 152 that correspond and cooperate with the external threads 142 such that they may be rotationally and/or removably coupled. According to some embodiments, the administration component 130 may be provided with the mounting collar 132 and the needle hub 150 partially engaged (e.g., with the threads 142, 152 being partially coupled), such as depicted in FIG. 1D. In some embodiments, the partial engagement (or first engagement state) may cause the administration member 170 (e.g., a second or proximal end thereof) to be positioned adjacent to (and/or in contact with) the puncture seal 140 of the mounting collar 132. In such a first engagement state, the administration component 130 may be coupled to the BFS vial 110, but the BFS vial 110 (and/or the puncture seal 140) have not yet been punctured and/or breached by the administration member 170.

According to some embodiments the needle hub 150 may couple to and/or retain the administration member 170. The administration member 170 may be inserted into and/or through the needle hub 150, for example, such that it comprises a first or administration end extending axially distal from the BFS vial 110 and a second or piercing end disposed within the needle hub 150. In some embodiments, the administration end and/or a distal portion of the administration member 170 may be housed, shrouded, and/or covered by the cap 180. According to some embodiments, the cap 180 may be configured to house the administration member 170 and to removably couple to the housing 150 (e.g., by fitting over an external portion thereof and/or by engaging with the external flange 144).

According to some embodiments, the mounting collar 132 and needle hub 150 combination may be utilized to couple and/or mate the administration member 170 with the BFS vial 110 to provide a mechanism via which the administration member 170 may be coupled to the soft plastic BFS vial 110 in a reliable manner. Due to the nature of the BFS plastic and/or process and/or the small form-factor of the BFS vial 110, for example, providing standard external threads (not shown) directly on the neck 112 would not be a viable option for it would result in an imprecise, unreliable, and/or non-water tight coupling (i.e., the threads would be deformable even if they could be properly manufactured to within the desired tolerances, which itself is not a likely result) between he BFS vial 110 and, e.g., the needle hub 150. Applicant has realized, for example, that "soft" plastics required for the BFS process are not susceptible to machining due to heat deformation of machined features during formation attempts as well as deformation due to mechanical stress during utilization. As such, standardized screw-on needle hubs (not shown; although similar to the needle hub 150, in some embodiments) are not readily compatible for attachment to BFS vials 110 (e.g., in the absence of the mounting collar 132).

In some embodiments, the administration member 170 may include a needle shaped and/or sized for at least one of subcutaneous, intramuscular, intradermal, and intravenous injection of the fluid agent into the patient. For ease of explanation and description, the figures and the description herein generally refer to the administration member 170 as a needle or cannula. However, it should be noted that, in other embodiments, the administration member 170 may include a nozzle (not shown) configured to control administration of the fluid agent to the patient. The nozzle may include a spray nozzle, for example, configured to facilitate dispersion of the fluid agent into a spray. Accordingly, a needle hub 150 fitted with a spray nozzle may be particularly useful in the administration of a fluid agent into the nasal passage, for example, or other parts of the body that benefit from a spray application (e.g., ear canal, other orifices). In other embodiments, the nozzle may be configured to facilitate formation of droplets of the fluid agent. Thus, a needle hub 150 including a droplet nozzle may be useful in the administration of a fluid agent by way of droplets, such as administration to the eyes, topical administration, and the like.

As generally understood, the fluid or drug (e.g., stored in the BFS vial 110 and/or one or more of the reservoirs 120, 122 thereof) agent may include any type of agent to be injected into a patient (e.g., animal such as a mammal, either human or non-human) and capable of producing an effect (alone, or in combination with an active ingredient). Accordingly, the agent may include, but is not limited to, a vaccine, a drug, a therapeutic agent, a medicament, a diluent, and/or the like. According to some embodiment, either or both of the fluid agent and the active ingredient (i.e., the drug agent and/or components thereof) may be tracked, monitored, checked for compatibility with each other, etc., such as by utilization of electronic data storage devices (not shown)

coupled to the various modules or components such as the BFS vial 110 (e.g., at, on, or in the identification area 124) and/or the administration component 130.

According to some embodiments, the mounting collar 132, the needle hub 150, and/or the cap 180 may be composed of a medical grade material. In some embodiments, the mounting collar 132, the needle hub 150, and/or the cap 180, may be composed of a thermoplastic polymer or other "hard" plastic (e.g., greater than 80 on the Rockwell "R" scale), including, but not limited to, polybenzimidazole, acrylonitrile butadiene styrene (ABS), polystyrene, polyvinyl chloride, or the like. In some embodiments, the pre-filled medical delivery assembly 100 may be advantageously manufactured (in mass quantities) in separate parts or portions, namely, at least the "soft" plastic BFS vial 110 portion (e.g., a "first" piece) and the "hard" plastic administration component 130 (e.g., the "second" piece), with such different plastic parts/portions being selectively coupled to administer a medication to a patient.

According to some embodiments, the pre-filled medical delivery assembly 100 may be advanced from the first engagement state to a second engagement state where the administration member 170 has pierced the BFS vial 110 and the fluid therein may readily be expressed through the administration member 170 (e.g., and into a patient). The partial engagement of the mounting collar 132 and the needle hub 150 (e.g., with the threads 142, 152 being partially coupled) as depicted in FIG. 1D may, for example, be transitioned to a more advanced, fully, or completely advanced state by application of a rotational force to the cap 180, e.g., as shown in FIG. 1D (at "C"). In some embodiments, the more advanced and/or full engagement (or second engagement state; as shown in FIG. 1E) may cause the administration member 170 (e.g., the second or proximal end thereof) to advance through the puncture seal 140 of the mounting collar 132 and through the seal 114 of the BFS vial 110. In such a manner, for example, the continued rotational engagement of the threads 142, 152 may cause the administration member 170 (e.g., the second or proximal end thereof) to open a fluid pathway between the BFS vial 110 (e.g., and/or the neck 112, and/or reservoirs 120, 122 thereof) and the first or distal end of the administration member 170. In some embodiments, the cap 180 may be utilized as a rotational force driver to transfer rotational force to the needle hub 150 to cause the advancement of the engagement of the threads 142, 152 (and, e.g., the puncturing of the puncture seal 140 and the seal 114 of the BFS vial 110).

In some embodiments, fewer or more components 110, 112, 114, 116, 118, 120, 122, 124, 130, 132, 134, 136, 138, 140, 142, 144, 150, 152, 170, 180 and/or various configurations of the depicted components 110, 112, 114, 116, 118, 120, 122, 124, 130, 132, 134, 136, 138, 140, 142, 144, 150, 152, 170, 180 may be included in the pre-filled medical delivery assembly 100 without deviating from the scope of embodiments described herein. In some embodiments, the components 110, 112, 114, 116, 118, 120, 122, 124, 130, 132, 134, 136, 138, 140, 142, 144, 150, 152, 170, 180 may be similar in configuration and/or functionality to similarly named and/or numbered components as described herein. According to some embodiments, the pre-filled medical delivery assembly 100 may comprise the mounting flange 116 but not the collapsible reservoir 120. In some embodiments, the pre-filled medical delivery assembly 100 may comprise the mounting flange 116 but not the dispensing reservoir 122. According to some embodiments, the administration component 130 may be provided without (and/or separately from) the BFS vial 110.

Referring now to FIG. 2A, FIG. 2B, FIG. 2C, FIG. 2D, FIG. 2E, FIG. 2F, and FIG. 2G, various views of a pre-filled medical delivery assembly coupling 232 (e.g., a connector made of "hard" plastic and configured to securely mate with a "soft" plastic BFS object/container) according to some embodiments are shown. The coupling 232 may comprise similar features and/or configurations and/or may be similar to the mounting collar 132 of FIG. 1A, FIG. 1B, FIG. 1C, FIG. 1D, FIG. 1E, and/or FIG. 1F. The coupling 232 may comprise and/or define, for example, a chamber, void, volume, and/or mounting bore 232-1, a top surface 232-2, and/or one or more mounting features 236. In some embodiments, the mounting bore 232-1 may be shaped to accept and/or retain a neck of a BFS vial (not shown; e.g., the neck 112 of FIG. 1A, FIG. 1B, FIG. 1C, FIG. 1D, FIG. 1E, and/or FIG. 1F herein), e.g., by defining various internal dimensions and/or features. The mounting bore 232-1 may comprise and/or define, for example, various interior diameters, each defined over different portions of the mounting bore 232-1. According to some embodiments, the mounting bore 232-1 may comprise and/or define an internal seat 238 that is specially located, sized, and/or shaped to accept a mounting flange (not shown; e.g., the "doughnut" shaped mounting flange 116 of FIG. 1A, FIG. 1B, FIG. 1C, FIG. 1D, FIG. 1E, and/or FIG. 1F herein). In some embodiments, the internal seat 238 may comprise an interior groove, channel, and/or seat that comprises and/or defines various physical dimensions and/or features such as a mating length, a seat depth, and/or a rounding radius. According to some embodiments, the mounting bore 232-1 may comprise an effluent passage disposed, formed, and/or cut into a second end thereof, but blocked by a seal 240.

According to some embodiments, the coupling 232 may be axially engaged to couple with a BFS vial (not shown; e.g., the BFS vial 110 of FIG. 1A, FIG. 1B, FIG. 1C, FIG. 1D, FIG. 1E, and/or FIG. 1F herein) via application of an axial mating force. A seal (not shown; e.g., the seal 134 of FIG. 1A, FIG. 1B, FIG. 1C, FIG. 1D, FIG. 1E, and/or FIG. 1F herein) covering the mounting bore 232-1 may be removed, for example, and the coupling 232 may be urged onto the neck of the BFS vial such that the cooperatively shaped internal seat 238 accepts the mounting flange of the BFS vial, thereby selectively and/or removably coupling the BFS vial to the coupling 232. In some embodiments (not shown), the internal seat 238 (and/or other interior features) and/or the mounting flange may be shaped such that uncoupling of the BFS vial and the coupling 232 is mechanically prohibited. According to some embodiments, the neck of the BFS vial may be advanced into the mounting bore 232-1 at a first portion thereof having a first interior diameter. In some embodiments, the neck may continue to advance into a second portion of the mounting bore 232-1 at a second portion thereof having the second interior diameter. As depicted, the second interior diameter may be smaller than the first interior diameter. According to some embodiments, the second interior diameter may be sized to accept an outer diameter of the BFS vial neck, which may continue to be inserted into the mounting bore 232-1.

In some embodiments, once the mounting flange (e.g., exterior rounded and/or axially elongated flange) of the BFS vial reaches the second portion having the second interior diameter, the mounting flange may engage with the side walls at the juncture/transition between the first interior diameter and the second interior diameter. The first interior diameter may be sized, for example, to be larger than the radial extents of the mounting flange, but the second interior diameter may be sized smaller than the radial extents, causing an engagement thereof. In some embodiments, such as depicted (but not separately labeled), an interior taper may be provided between the first interior diameter and the second interior diameter, such that the mounting flange may engage along the taper, before the second portion with the second interior diameter is reached.

According to some embodiments, the BFS vial may be softer than (e.g., have a lower hardness rating and/or be elastic) the material of the coupling 232, which may cause the mounting flange to deflect radially inward upon engagement (and continued application of axial force) with the inside walls/surfaces of the mounting bore 232-1. The mounting flange may deform, compress, and/or flatten to pass through the second portion having the second interior diameter, for example, and may advance into the internal seat 238.

According to some embodiments, once the mounting flange of the BFS vial passes into the internal seat 238, the mounting flange may expand radially outward to (or near) the original axial extents thereof (e.g., releasing the elastic potential energy stored by the elastic deformation thereof). In some embodiments, such as in the case that the internal seat 238 is sized to be slightly smaller (e.g., one half to two percent (0.5%-2.0%)) than the mounting flange, the mounting flange may be able to reform only to near its original extents, thereby causing the mounting flange to retain some stored elastic energy due to continued (although small) deformation thereof. Such retained deformation may, for example, cause an interference pressure to remain between the mounting flange and the inside walls of the internal seat 238 such that the fit between the materials remains tight and substantially leakproof. In some embodiments, the configuration of the internal seat 238 and/or of the mounting bore 232-1 may be defined to be cooperative with a specifically sized BFS vial or bottle (e.g., the BFS vial 110 of FIG. 1A, FIG. 1B, FIG. 1C, FIG. 1D, FIG. 1E, and/or FIG. 1F herein) such that the mating thereof may be accomplished via a steady, uniform application of a mating force that both reduces strain on the components as well as provides for a successful and repeatable user experience.

According to some embodiments, the first interior diameter may be sized between seven and forty-five hundredths millimeters and nine millimeters (7.45-mm to 9-mm). In some embodiments, the second interior diameter may be sized between six and a half millimeters and seven millimeters (6.5-mm to 7-mm). According to some embodiments, the third interior diameter may be sized equal to the second interior diameter or may be sized smaller. The third interior diameter may be sized, for example, between six millimeters and six and a half millimeters (6-mm to 6.5-mm). In some embodiments, the mating length, seat depth, and/or rounding radius may be sized cooperatively with the mounting flange of the BFS vial. According to some embodiments, the mating length may be sized between three and four millimeters (3-mm to 4-mm), the seat depth may be sized between sixty-five hundredths and nine tenths millimeters (0.65-mm to 0.8-mm), and/or the rounding radius may be between four and five millimeters (4-mm to 5-mm).

In some embodiments, the coupling 232 may comprise and/or define external threads 242 disposed on and/or about a second end thereof. According to some embodiments, the coupling 232 may comprise one or more thread interruptions 242-1 that provide for areas of increased wall thickness to reduce the likelihood of structural failure in the case that the threads 242 receive a rotational force (e.g., torque) when mated with a corresponding object (not shown; e.g., the needle hub 150 of FIG. 1A, FIG. 1B, FIG. 1C, FIG. 1D, FIG. 1E, and/or FIG. 1F herein). In some embodiments, a pathway into through the mounting bore 232-1 and into the internal seat 238 may be modified from a simply circular cross-section to provide for easier entry of an inserted mounting flange. In some embodiments, for example, the interior passage may comprise a plurality of radially-spaced undercuts that locally increase the interior diameter of the passage to provide less friction to a mounting flange urged inward toward the internal seat 238.

According to some embodiments, the coupling 232 may comprise and/or define one or more external flanges 244. The exterior flange 244 depicted, for example, may define a stop surface that limits the extent of axial mating of the coupling 232 with other objects and/or components (not shown; such as the needle hub 150 of FIG. 1A, FIG. 1B, FIG. 1C, FIG. 1D, FIG. 1E, and/or FIG. 1F herein). In the case that a needle hub is threaded onto the coupling 232, for example, the exterior flange 244 may engage with a portion of the needle hub to prevent axial advancement and/or thread engagement beyond the exterior flange 244.

In some embodiments, fewer or more components 232-1, 232-2, 236, 238, 240, 242, 242-1, 244 and/or various configurations of the depicted components 232-1, 232-2, 236, 238, 240, 242, 242-1, 244 may be included in the pre-filled medical delivery assembly coupling 232 without deviating from the scope of embodiments described herein. In some embodiments, the components 232-1, 232-2, 236, 238, 240, 242, 242-1, 244 may be similar in configuration and/or functionality to similarly named and/or numbered components as described herein.

III. Pre-Filled Medical Delivery Assemblies—Interior Threaded Coupling and Safety Shield Turning to FIG. 3A, FIG. 3B, FIG. 3C, FIG. 3D, FIG. 3E, FIG. 3F, and FIG. 3G, various views of a pre-filled medical delivery assembly 300 according to some embodiments are shown. In some embodiments, the pre-filled medical delivery assembly 300 may comprise various inter-connected and/or modular components such as a BFS vial 310 comprising and/or defining a vial neck 312, a fluid seal 314, a mounting flange 316, a bottle flange 318, a collapsible reservoir 320, a dispensing reservoir 322, and/or an identification area 324. According to some embodiments, the pre-filled medical delivery assembly 300 may comprise an administration (e.g., injection) module or component 330 that is manufactured, assembled, and/or provided as a separate unit from the BFS vial 310. In some embodiments, the administration component 330 may comprise a mounting collar 332 which itself comprises, is coupled to, and/or defines various features and/or elements. The mounting collar 332 and/or the administration assembly 330 may, for example, be maintained as a closed and/or sterile component via a seal 334 (e.g., a foil, wax, paper, and/or other thin, pierceable, tear-able, and/or removable object or layer coupled to the mounting collar 332 and/or the administration component 330) that seals an interior volume or socket 332-1 (labeled in FIG. 3G) of the mounting collar 332, disposed at a first end thereof. In some embodiments, the mounting collar 332 may comprise and/or define a needle hub socket 332-3 disposed at a second end thereof. According to some embodiments, the mounting collar 332 may comprise one or more coupling or mounting features 336 (e.g., internal grooves and/or seats), an internal seat 338 (e.g., that is configured to accept the mounting flange 316 of the BFS vial 310 in the case that the neck 312 of the BFS vial 310 is inserted into the mounting collar 332 and/or the administration component 330), a puncture seal 340, and/or internal threads 342 (e.g., disposed and/or formed within the needle hub socket 332-3). In some embodiments, the mounting collar 332 may comprise and/or define an exterior flange 344 (e.g., a radial flange) that is operable to receive, mate with, and/or otherwise engage with a needle hub 350. According to some embodiments, the needle hub 350 may couple to the mounting collar 332 via external threads 352 thereof that correspond to and/or mate with the internal threads 342 of the mounting collar 332. In some embodiments, the needle hub 350 may comprise an external groove, projection, and/or drive surface 354-1 that may be rotationally engaged to manipulate the coupling of the threads 342, 352. According to some embodiments, the needle hub 350 (and/or a riser 356 thereof) may comprise, couple to and/or house a needle, cannula, and/or other administration member 370, and/or a cap 380 (e.g., selectively engaged and/or coupled to the needle hub 350 to shroud, house, and/or protect the administration member 370).

In some embodiments, the administration component 330 may comprise and/or be coupled to a safety shield 390. The safety shield 390 may comprise, for example, a shield base 392 that is mounted on and/or around the neck 312 of the BFS vial 310. According to some embodiments, the shield base 392 may comprise and/or be coupled to a hinge element 392-1 and/or may comprise one or more mounting features 394. The hinge element 392-1 may flexibly couple the shield base 392 to a shield element 396, for example, the shield element 396 comprising a molded and/or shaped element configured to selectively cover the administration member 370. In some embodiments, the shield element 396 may comprise and/or define a shield volume or space 398 that is sized and/or shaped to accept and/or house the administration member 370. In some embodiments, the shield space 398 may comprise, define, and/or house a needle keeper 398-1, e.g., in the case that the administration member 37—comprises a needle and/or cannula. According to some embodiments, the pre-filled medical delivery assembly 300 may include a modular design consisting of separately constructed components 310, 330, 332, 350, 370, 380, 390 cooperatively arranged and coupled to one another.

In some embodiments, the collapsible reservoir 320 may be filled (fully or partially) with a fluid or other agent (not separately shown) to be delivered, e.g., to a patient (not shown). According to some embodiments, the fluid may be injected into the BFS vial 310 in a sterile environment during manufacture via a BFS process and sealed within the BFS vial 310 via the fluid seal 314. The fluid seal 314 may comprise a portion of the molded BFS vial 310 for example that is configured to be pierced to expel the fluid, e.g., such as by providing a flat or planar piercing surface and/or by being oriented normal to an axis of the BFS vial 310 (and/or the pre-filled medical delivery assembly 300). In some embodiments, the fluid seal 314 may comprise a foil, wax, paper, and/or other thin, pierceable object or layer coupled to the BFS vial 310. In some embodiments, the neck 312 of the BFS vial 310 may comprise the mounting flange 316 such as, e.g., the "doughnut"-shaped exterior flange depicted. The mounting flange 316 may, for example, provide a radially elastic mating surface that is operable to provide a selective engagement or fit within the socket 332-1 of the administration component 330.

According to some embodiments, the fluid may generally pass between the collapsible reservoir 320 and the connected dispensing reservoir 322. In some embodiments, a juncture, valve, and/or passage (not separately labeled) between the dispensing reservoir 322 and the collapsible reservoir 320 may restrict flow such that the fluid may readily enter one of the dispensing reservoir 322 and the collapsible reservoir 320 but may not readily return to the other reservoir 320, 322. Such a constriction may in some embodiments, provided advantages as described herein. In some embodiments, the constriction may not be necessary or desirable, such as in the case that the collapsible reservoir 320 and the dispensing reservoir 322 are formed and/or combined as a single, unobstructed reservoir, e.g., a single fluid reservoir (not shown).

Figures 3A, 3B, 3C:
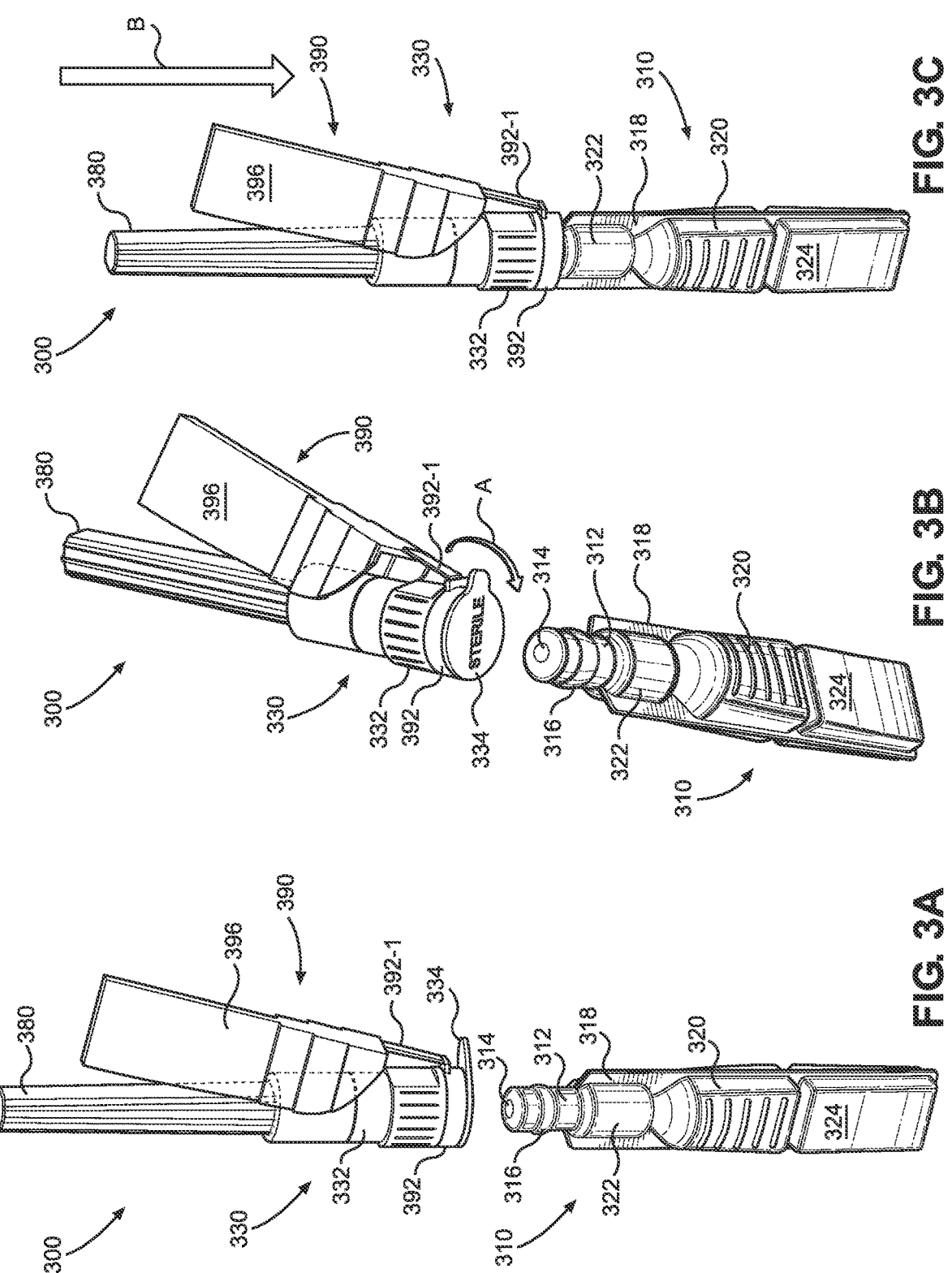
FIG. 3A, FIG. 3B, FIG. 3C, FIG. 3D, FIG. 3E, FIG. 3F, and FIG. 3G are various views of a pre-filled medical delivery assembly according to some embodiments.

In some embodiments, the pre-filled medical delivery assembly 300 may include a modular design consisting of separately constructed components 310, 330 cooperatively arranged and coupled to one another. As depicted in FIG. 3A, for example, the BFS vial 310 and the administration component 330 may be manufactured, packaged, shipped, stored, and/or provided as separate components. In such a manner, the administration component 330 may not need to be stored or shipped in accordance with often restrictive requirements imposed on medicaments and may accordingly reduce the amount of space required for such specialized storage and/or shipping. The administration component 330 may also or alternatively be manufactured, stored, and/or shipped in advance (e.g., at a first time) while the BFS vial 310 that is pre-filled with the fluid may be manufactured, stored, and/or shipped at a later time (e.g., a second time). In some embodiments, the delay between the first time and the second time may be lengthy without causing detrimental effects, as the administration component 330 may be stored, in some embodiments, indefinitely. In such a manner, units of the administration component 330 may be provided to be on-hand in advance of the availability and/or arrival of the BFS vial 310, reducing supply chain constraints in the case of proactive administration component 330 procurement.

According to some embodiments, the components 310, 330 may be coupled, e.g., in the field and/or in situ, to provide an active pre-filled (e.g., injectable) medical delivery device. As shown in FIG. 3B, for example, the seal 334 may be removed from the administration component 330 (and/or the shield base 392; at "A") and the administration component 330 (and/or the socket 332-1 and/or the shield base 392 thereof) may be aligned with the neck 312 of the BFS vial 310. According to some embodiments, the administration component 330 (and/or the mounting collar 332 and/or the shield base 392 thereof) may be axially engaged to couple with the BFS vial 310 via application of a mating axial force, as shown in FIG. 3C (at "B"). The administration component 330 (and/or the mounting collar 332 and/or the shield base 392 thereof) may be urged onto the neck 312 of the BFS vial 310, for example, such that the cooperatively shaped internal seat 338 (e.g., an interior groove or channel) accepts the mounting flange 316, thereby removably coupling the BFS vial 310 and the administration component 330 (and/or the mounting collar 332 and/or the shield base 392 thereof). In some embodiments, the internal seat 338 (and/or other interior features) and/or the mounting flange 316 may be shaped such that uncoupling of the BFS vial 310 and the administration component 330 (and/or the mounting collar 332 and/or the shield base 392 thereof) is mechanically prohibited. In some embodiments, the mounting flange 316 may be shaped as an axially elongated rounded exterior flange (e.g., the "doughnut" shape as depicted) and/or the internal seat 338 may comprise a cooperative and/or mirrored axially elongated rounded interior groove or track. According to some embodiments, the one or more mounting features 336 such as the interior radially-spaced grooves depicted may engage with the bottle flange 318 (and/or portions of the BFS vial 310) in a case where the safety shield 390 is not utilized, such that rotation of the administration component 330 (and/or the mounting collar 332 thereof) with respect to the BFS vial 310 is restricted in the case that they are coupled. In some embodiments, the one or more mounting features 336 such as the interior radially-spaced grooves depicted may engage with the mounting features 394 of the safety shield 390 (and/or portions of the shield base 392) in a case where the safety shield 390 is utilized and is disposed between the BFS vial 310 and the administration component 330, such that rotation of the administration component 330 (and/or the mounting collar 332 thereof) with respect to the BFS vial 310 is not restricted in the case that they are coupled. In some embodiments, such as in the case that the mounting features 394 of the safety shield 390 engage with, are seated in, and/or are retained by corresponding mounting features 336 of the mounting collar 332, axial rotation of the mounting collar 332 with respect to the safety shield 390 may be mechanically prohibited. In some embodiments, the mounting features 396 of the safety shield 390 may not be utilized (or may comprise one or more continuous and/or non-rotation limiting features) and free rotation between the mounting collar 332 and the safety shield 390 may be mechanically permitted. According to some embodiments, the coupling of the BFS vial 310 and the administration component 330 (and/or the mounting collar 332 and/or the safety shield 390 thereof) may be configured to explicitly permit free rotation (e.g., about a common axis) of the BFS vial 310 with respect to the administration component 330 (and/or the mounting collar 332 and/or the safety shield 390 thereof). The mounting features 336 may not, in some embodiments for example, engage with the BFS vial 310 (and/or the mounting flange 316 thereof), e.g., to permit rotation therebetween.

Figure 3E:
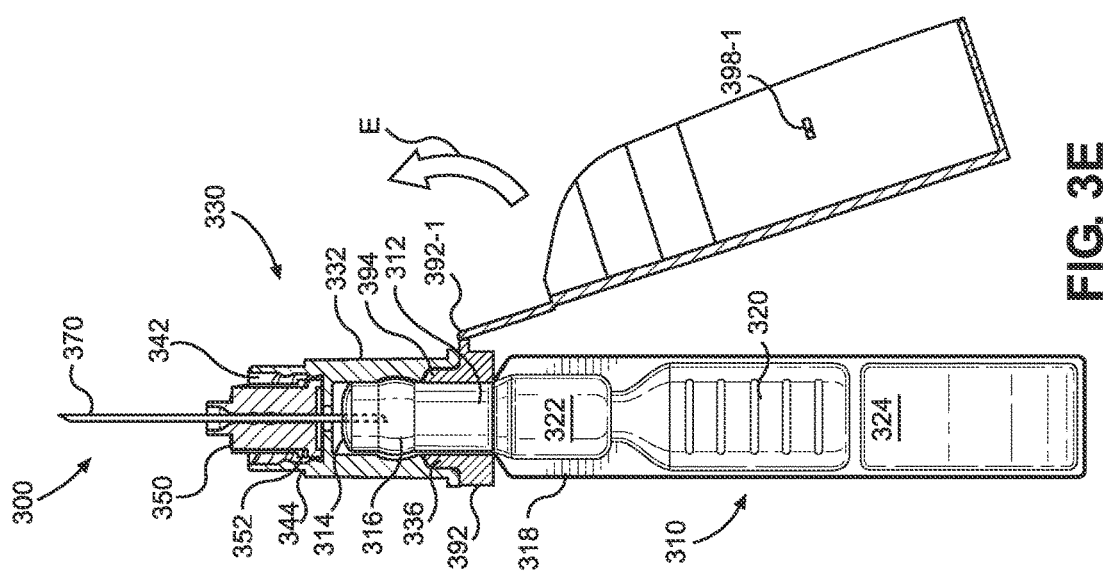
Figure 3D:
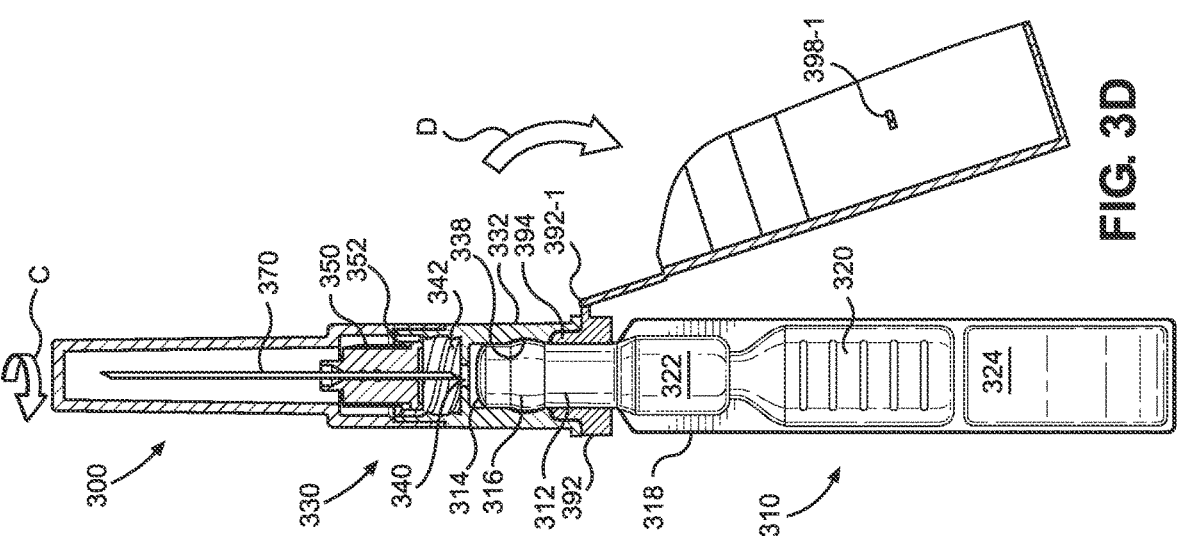

As depicted in FIG. 3D, in some embodiments the neck 312 of the BFS vial 330 may be urged and/or forced into the socket 332-1 of the mounting collar 332 (and/or through the shield base 392, e.g., which may be annular in shape as depicted) until the mounting flange 316 becomes seated in (and/or coupled to or mated with) the internal seat 338 (e.g., a seated position). In such a manner, the fluid seal 314 may be advantageously positioned adjacent to the puncture seal 340. According to some embodiments, the mounting flange 316 may be configured as the doughnut shape (as depicted) to provide various advantages to the pre-filled medical delivery assembly 300. The axial elongation of the mounting flange 316 may, for example, provide for a smooth, uniform, and/or less forceful mating process that is less likely to deform the soft plastic neck 312 of the BFS vial 310 and/or may provide for a lengthened mating surface that is more likely to prevent leakage of the fluid. In some embodiments, the mounting flange 316 and the cooperatively shaped and sized internal seat 338 may permit simple, effective, and/or economic attachment of the administration component 330 to the BFS vial 310. According to some embodiments, e.g., in preparation for administration and/or utilization of the pre-filled medical delivery assembly 300, the shield element 396 of the safety shield 390 may be rotated, flipped, and/or otherwise repositioned via activation of the hinge element 392-1 (at "D").

In some embodiments, the needle hub 350 may be coupled to the mounting collar 332 via engagement of the internal threads 342 of the mounting collar 332 with the external threads 352 (or thread) of the needle hub 350. The external threads 352 that correspond and cooperate with the internal threads 342 such that they may be rotationally and/or removably coupled. According to some embodiments, the administration component 330 may be provided with the mounting collar 332 and the needle hub 350 partially engaged (e.g., with the threads 342,352 being partially coupled), such as depicted in FIG. 3D. In some embodiments, the partial engagement (or first engagement state) may cause the administration member 370 (e.g., a second or proximal end thereof) to be positioned adjacent to (and/or in contact with) the puncture seal 340 of the mounting collar 332. In such a first engagement state, the administration component 330 may be coupled to the BFS vial 310, but the BFS vial 310 (and/or the puncture seal 340) have not yet been punctured and/or breached by the administration member 370.

According to some embodiments the needle hub 350 may couple to and/or retain the administration member 370. The administration member 370 may be inserted into and/or through the needle hub 350 (and/or the riser 356 thereof), for example, such that it comprises a first or administration end extending axially distal from the BFS vial 310 and a second or piercing end disposed within the needle hub 350. In some embodiments, the administration end and/or a distal portion of the administration member 370 may be housed, shrouded, and/or covered by the cap 380. According to some embodiments, the cap 380 may be configured to house the administration member 370 and to removably couple to the housing 350 (e.g., by fitting over an external portion thereof and/or by engaging with the external flange 344).

According to some embodiments, the mounting collar 332 and needle hub 350 (and cap 380) combination may be utilized to couple and/or mate the administration member 370 with the BFS vial 310 to provide a mechanism via which the administration member 370 may be coupled to the soft plastic BFS vial 310 in a reliable manner. Due to the nature of the BFS plastic and/or process and/or the small form-factor of the BFS vial 310, for example, providing standard external threads (not shown) directly on the neck 312 would not be a viable option for it would result in an imprecise, unreliable, and/or non-water tight coupling (i.e., the threads would be deformable even if they could be properly manu-factured to within the desired tolerances, which itself is not a likely result) between he BFS vial 310 and, e.g., the needle hub 350. Applicant has realized, for example, that "soft" plastics required for the BFS process are not susceptible to machining due to heat deformation of machined features during formation attempts as well as deformation due to mechanical stress during utilization. As such, standardized screw-on needle hubs (not shown) are not readily compat-ible for attachment to BFS vials 310 (e.g., in the absence of the mounting collar 332).

In some embodiments, the administration member 370 may include a needle shaped and/or sized for at least one of subcutaneous, intramuscular, intradermal, and intravenous injection of the fluid agent into the patient. For ease of explanation and description, the figures and the description herein generally refer to the administration member 370 as a needle or cannula. However, it should be noted that, in other embodiments, the administration member 370 may include a nozzle (not shown) configured to control admin-istration of the fluid agent to the patient. The nozzle may include a spray nozzle, for example, configured to facilitate dispersion of the fluid agent into a spray. Accordingly, a needle hub 350 fitted with a spray nozzle may be particularly useful in the administration of a fluid agent into the nasal passage, for example, or other parts of the body that benefit from a spray application (e.g., ear canal, other orifices). In other embodiments, the nozzle may be configured to facili-tate formation of droplets of the fluid agent. Thus, a needle hub 350 including a droplet nozzle may be useful in the administration of a fluid agent by way of droplets, such as administration to the eyes, topical administration, and the like.

As generally understood, the fluid or drug (e.g., stored in the BFS vial 310 and/or one or more of the reservoirs 320, 322 thereof) agent may include any type of agent to be injected into a patient (e.g., animal such as a mammal, either human or non-human) and capable of producing an effect (alone, or in combination with an active ingredient). Accordingly, the agent may include, but is not limited to, a vaccine, a drug, a therapeutic agent, a medicament, a diluent, and/or the like. According to some embodiment, either or both of the fluid agent and the active ingredient (i.e., the drug agent and/or components thereof) may be tracked, monitored, checked for compatibility with each other, etc., such as by utilization of electronic data storage devices (not shown) coupled to the various modules or components such as the BFS vial 310 (e.g., at, on, or in the identification area 324) and/or the administration component 330.

According to some embodiments, the mounting collar 332, the needle hub 350, and/or the cap 380 may be composed of a medical grade material. In some embodiments, the mounting collar 332, the needle hub 350, and/or the cap 380, may be composed of a thermoplastic polymer or other "hard" plastic (e.g., greater than 80 on the Rockwell "R" scale), including, but not limited to, polybenzimidazole, ABS, polystyrene, polyvinyl chloride, or the like. In some embodiments, the pre-filled medical delivery assembly 300 may be advantageously manufactured (in mass quantities) in separate parts or portions, namely, at least the "soft" plastic BFS vial 310 portion (e.g., a "first" piece) and the "hard" plastic administration component 330 (e.g., the "second" piece), with such different plastic parts/portions being selectively coupled to administer a medication to a patient.

According to some embodiments, the pre-filled medical delivery assembly 300 may be advanced from the first engagement state to a second engagement state where the administration member 370 has pierced the BFS vial 310 and the fluid therein may readily be expressed through the administration member 370 (e.g., and into a patient). The partial engagement of the mounting collar 332 and the needle hub 350 (e.g., with the threads 342, 352 being partially coupled) as depicted in FIG. 3D may, for example, be transitioned to a more advanced, fully, or completely advanced state by application of a rotational force to the cap 380, e.g., as shown in FIG. 3D (at "C"). In some embodiments, the more advanced and/or full engagement (or second engagement state; as shown in FIG. 3E) may cause the administration member 370 (e.g., the second or proximal end thereof) to advance through the puncture seal 340 of the mounting collar 332 and through the seal 314 of the BFS vial 310. In such a manner, for example, the continued rotational engagement of the threads 342, 352 may cause the administration member 370 (e.g., the second or proximal end thereof) to open a fluid pathway between the BFS vial 310 (e.g., and/or the neck 312, and/or reservoirs 320, 322 thereof) and the first or distal end of the administration member 370. In some embodiments, the cap 380 may be utilized as a rotational force driver to transfer rotational force to the needle hub 350 to cause the advancement of the engagement of the threads 342, 352 (and, e.g., the puncturing of the puncture seal 340 and the seal 314 of the BFS vial 310). The inside of the cap 380 may comprise a driver element (not shown), for example, that is sized and/or shaped to engage with the drive surface 354-1 of the needle hub 350 such that rotational force applied to the cap 380 is transferred to and rotationally advances the needle hub 350. In such a manner, for example, the cap 380 may be utilized to complete the threading/mating of the threads 342, 352 and thereby causing the second or proximal end of the administration member 370 to pierce each of the puncture seal 340 and the seal 314 of the BFS vial 310. According to some embodiments, one or more of the reservoirs 320, 322 may be compressed (e.g., via application of radially inward force) to expel the fluid therein through the administration member 370. In some embodiments, once the administration is complete, the shield element 396 of the safety shield 390 may be repositioned (e.g., via activation and/or utilization of the hinge element 392-1) such as by flipping the shield element 396 (at "E" in FIG. 3E) to cover the administration member 370—e.g., as depicted in FIG. 3F.

In some embodiments, fewer or more components 310, 312, 314, 316, 318, 320, 322, 324, 330, 332, 332-1, 334, 336, 338, 340, 342, 344, 350, 352, 354-1, 356, 370, 380, 390, 392, 392-1, 394, 396, 398, 398-1 and/or various configurations of the depicted components 310, 312, 314, 316, 318, 320, 322, 324, 330, 332, 332-1, 334, 336, 338, 340, 342, 344, 350, 352, 354-1, 356, 370, 380, 390, 392, 392-1, 394, 396, 398, 398-1 may be included in the pre-filled medical delivery assembly 300 without deviating from the scope of embodiments described herein. In some embodiments, the components 310, 312, 314, 316, 318, 320, 322, 324, 330, 332, 332-1, 334, 336, 338, 340, 342, 344, 350, 352, 354-1, 356, 370, 380, 390, 392, 392-1, 394, 396, 398, 398-1 may be similar in configuration and/or functionality to similarly named and/or numbered components as described herein. According to some embodiments, the pre-filled medical delivery assembly 300 may comprise the mounting flange 316 but not the collapsible reservoir 320. In some embodiments, the pre-filled medical delivery assembly 300 may comprise the mounting flange 316 but not the dispensing reservoir 322. According to some embodiments, the administration component 330 may be provided without (and/or separately from) the BFS vial 310. In some embodiments, the safety shield 390 may not be included and/or utilized.

Referring now to FIG. 4A, FIG. 4B, FIG. 4C, FIG. 4D, FIG. 4E, FIG. 4F, and FIG. 4G, various views of a pre-filled medical delivery assembly coupling 432 (e.g., a connector made of "hard" plastic and configured to securely mate with a "soft" plastic BFS object/container) according to some embodiments are shown. The coupling 432 may comprise similar features and/or configurations and/or may be similar to the mounting collar 332 of FIG. 3A, FIG. 3B, FIG. 3C, FIG. 3D, FIG. 3E, FIG. 3F, and/or FIG. 3G herein. The coupling 432 may comprise and/or define, for example, a chamber, void, volume, and/or mounting socket 432-1, a needle hub socket 432-3, and/or one or more mounting features 436. In some embodiments, the mounting socket 432-1 may be shaped to accept and/or retain a neck of a BFS vial (not shown; e.g., the neck 312 of FIG. 3A, FIG. 3B, FIG. 3C, FIG. 3D, FIG. 3E, FIG. 3F, and/or FIG. 3G herein), e.g., by defining various internal dimensions and/or features. The mounting socket 432-1 may comprise and/or define, for example, various interior diameters, each defined over different portions of the mounting socket 432-1. According to some embodiments, the mounting socket 432-1 may comprise and/or define an internal seat 438 that is specially located, sized, and/or shaped to accept a mounting flange (not shown; e.g., the "doughnut" shaped mounting flange 316 of FIG. 3A, FIG. 3B, FIG. 3C, FIG. 3D, FIG. 3E, FIG. 3F, and/or FIG. 3G herein). In some embodiments, the internal seat 438 may comprise an interior groove, channel, and/or seat that comprises and/or defines various physical dimensions and/or features such as a mating length, a seat depth, and/or a rounding radius. In some embodiments, the internal seat 438 may comprise an interior channel (e.g., a circumferential channel) that is rounded at a radius in the range of four to five millimeters (4-mm to 5-mm). In some embodiments, the internal seat 438 extends radially outward into an interior wall of the mounting socket 432-1 by a protrusion amount and wherein a length of the internal seat 438 is in the range of four and three tenths times (4.3×) and five and three tenths times (5.3×) the protrusion amount. According to some embodiments, the mounting socket 432-1 may comprise an effluent passage disposed, formed, and/or cut into a second end thereof, but blocked and/or interrupted by a seal 440.

According to some embodiments, the coupling 432 may be axially engaged to couple with a BFS vial (not shown; e.g., the BFS vial 310 of FIG. 3A, FIG. 3B, FIG. 3C, FIG. 3D, FIG. 3E, FIG. 3F, and/or FIG. 3G herein herein) via application of an axial mating force. A seal (not shown; e.g., the seal 334 of FIG. 3A, FIG. 3B, FIG. 3C, FIG. 3D, FIG. 3E, FIG. 3F, and/or FIG. 3G herein) covering the mounting socket 432-1 (and/or covering an opening of a safety shield base coupled to the coupling 432; not shown) may be removed, for example, and the coupling 432 may be urged onto the neck of the BFS vial such that the cooperatively shaped internal seat 438 accepts the mounting flange of the BFS vial, thereby selectively and/or removably coupling the BFS vial to the coupling 432. In some embodiments (not shown), the internal seat 438 (and/or other interior features) and/or the mounting flange may be shaped such that uncoupling of the BFS vial and the coupling 432 is mechanically prohibited. According to some embodiments, the neck of the BFS vial may be advanced into the mounting socket 432-1 at a first portion thereof having a first interior diameter. In some embodiments, the neck may continue to advance into a second portion of the mounting socket 432-1 at a second portion thereof having the second interior diameter. As depicted, the second interior diameter may be smaller than the first interior diameter. According to some embodiments, the second interior diameter may be sized to accept an outer diameter of the BFS vial neck, which may continue to be inserted into the mounting socket 432-1.

In some embodiments, once the mounting flange (e.g., exterior rounded and/or axially elongated flange) of the BFS vial reaches the second portion having the second interior diameter, the mounting flange may engage with the side walls at the juncture/transition between the first interior diameter and the second interior diameter. The first interior diameter may be sized, for example, to be larger than the radial extents of the mounting flange, but the second interior diameter may be sized smaller than the radial extents, causing an engagement thereof. In some embodiments, such as depicted (but not separately labeled), an interior taper may be provided between the first interior diameter and the second interior diameter, such that the mounting flange may engage along the taper, before the second portion with the second interior diameter is reached.

According to some embodiments, the BFS vial may be softer than (e.g., have a lower hardness rating and/or be elastic) the material of the coupling 432, which may cause the mounting flange to deflect radially inward upon engagement (and continued application of axial force) with the inside walls/surfaces of the mounting socket 432-1. The mounting flange may deform, compress, and/or flatten to pass through the second portion having the second interior diameter, for example, and may advance into the internal seat 438.

According to some embodiments, once the mounting flange of the BFS vial passes into the internal seat 438, the mounting flange may expand radially outward to (or near) the original axial extents thereof (e.g., releasing the elastic potential energy stored by the elastic deformation thereof). In some embodiments, such as in the case that the internal seat 438 is sized to be slightly smaller (e.g., one half to two percent (0.5%-2.0%)) than the mounting flange, the mounting flange may be able to reform only to near its original extents, thereby causing the mounting flange to retain some stored elastic energy due to continued (although small) deformation thereof. Such retained deformation may, for example, cause an interference pressure to remain between the mounting flange and the inside walls of the internal seat 438 such that the fit between the materials remains tight and substantially leakproof. In some embodiments, the configuration of the internal seat 438 and/or of the mounting socket 432-1 may be defined to be cooperative with a specifically sized BFS vial or bottle (e.g., the BFS vial 310 of FIG. 3A, FIG. 3B, FIG. 3C, FIG. 3D, FIG. 3E, FIG. 3F, and/or FIG. 3G herein) such that the mating thereof may be accomplished via a steady, uniform application of a mating force that both reduces strain on the components as well as provides for a successful and repeatable user experience.

According to some embodiments, the first interior diameter may be sized between seven and forty-five hundredths millimeters and nine millimeters (7.45-mm to 9-mm). In some embodiments, the second interior diameter may be sized between six and a half millimeters and seven millimeters (6.5-mm to 7-mm). According to some embodiments, the third interior diameter may be sized equal to the second interior diameter or may be sized smaller. The third interior diameter may be sized, for example, between six millimeters and six and a half millimeters (6-mm to 6.5-mm). In some embodiments, the mating length, seat depth, and/or rounding radius may be sized cooperatively with the mounting flange of the BFS vial. According to some embodiments, the mating length may be sized between three and four millimeters (3-mm to 4-mm), the seat depth may be sized between sixty-five hundredths and nine tenths millimeters (0.65-mm to 0.8-mm), and/or the rounding radius may be between four and five millimeters (4-mm to 5-mm).

In some embodiments, the coupling 432 may comprise and/or define internal threads 442 disposed in and/or about the needle hub socket 432-3 at the second end of the coupling 432. According to some embodiments, a pathway into and/or through the mounting socket 432-1 and into the internal seat 438 may be modified from a simply circular cross-section to provide for easier entry of an inserted mounting flange. In some embodiments, for example, the interior passage may comprise a plurality of radially-spaced undercuts that locally increase the interior diameter of the passage to provide less friction to a mounting flange urged inward toward the internal seat 438.

According to some embodiments, the coupling 432 may comprise and/or define one or more external flanges 444. The exterior flange 444 depicted, for example, may define a stop surface that limits the extent of axial mating of the coupling 432 with other objects and/or components (not shown; such as the cap 380 of FIG. 3A, FIG. 3B, FIG. 3C, FIG. 3D, FIG. 3E, FIG. 3F, and/or FIG. 3G herein). In the case that a needle hub is threaded into the coupling 432 (e.g., into the needle hub socket 432-3 thereof), for example, and/or a cap (not shown) is sleeved over the coupling 432, the exterior flange 444 may engage with a portion of the cap to prevent axial advancement beyond the exterior flange 444.

Figure 3G:
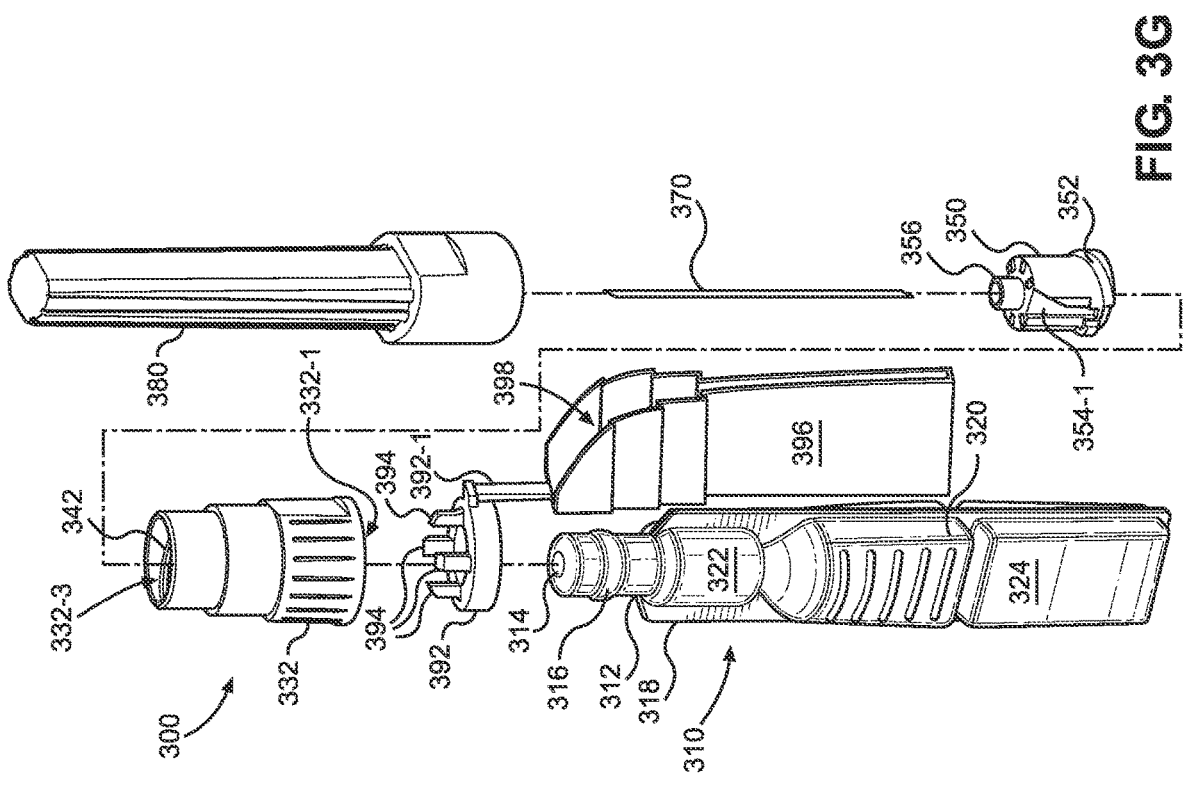
Figure 3F:
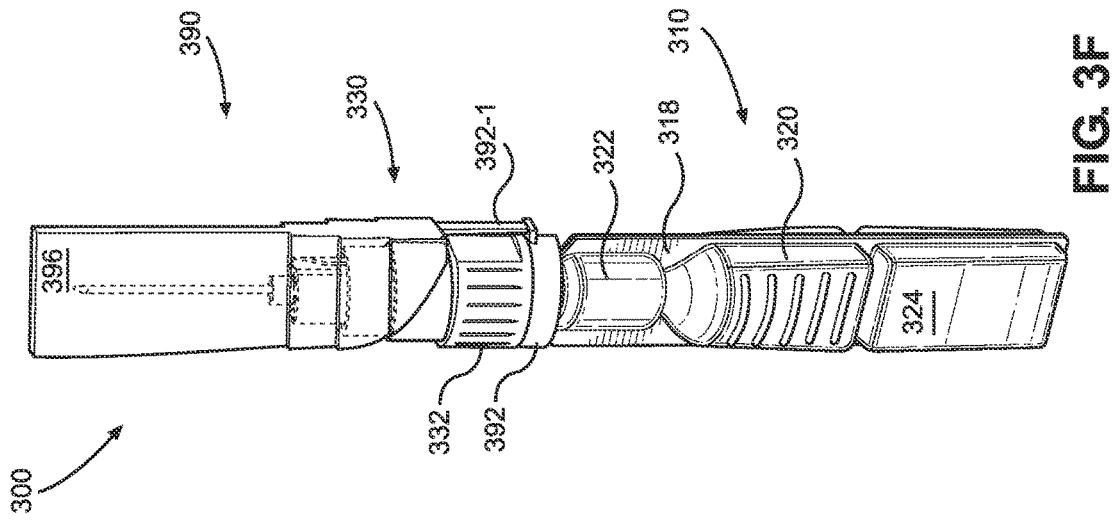
Figures 4A, 4B, 4C, 4D, 4E, 4F, 4G:
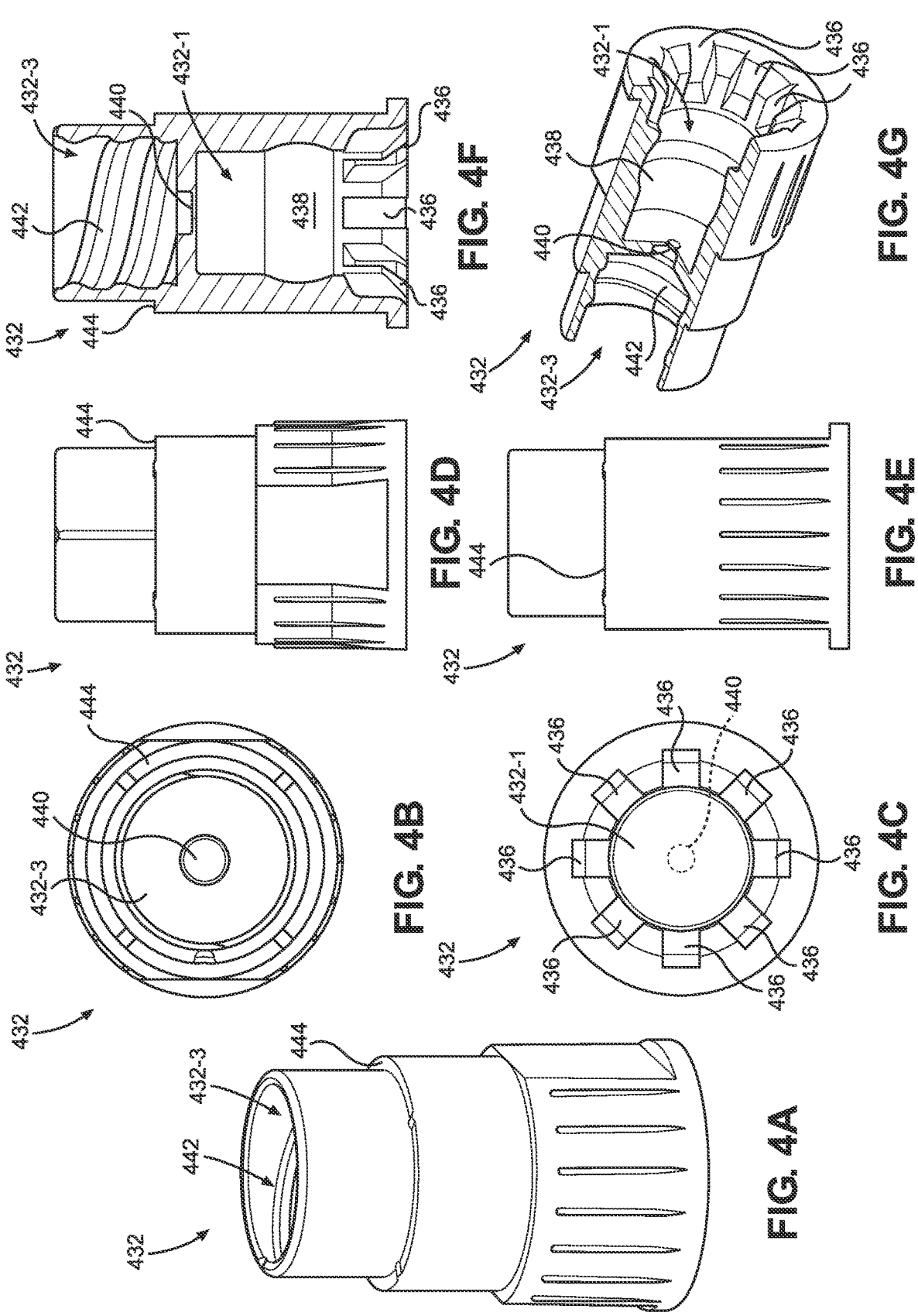
FIG. 4A, FIG. 4B, FIG. 4C, FIG. 4D, FIG. 4E, FIG. 4F, and FIG. 4G are various views of a pre-filled medical delivery assembly coupling according to some embodiments.
Figures 5A, 5B, 5C, 5D, 5E, 5F, 5G:
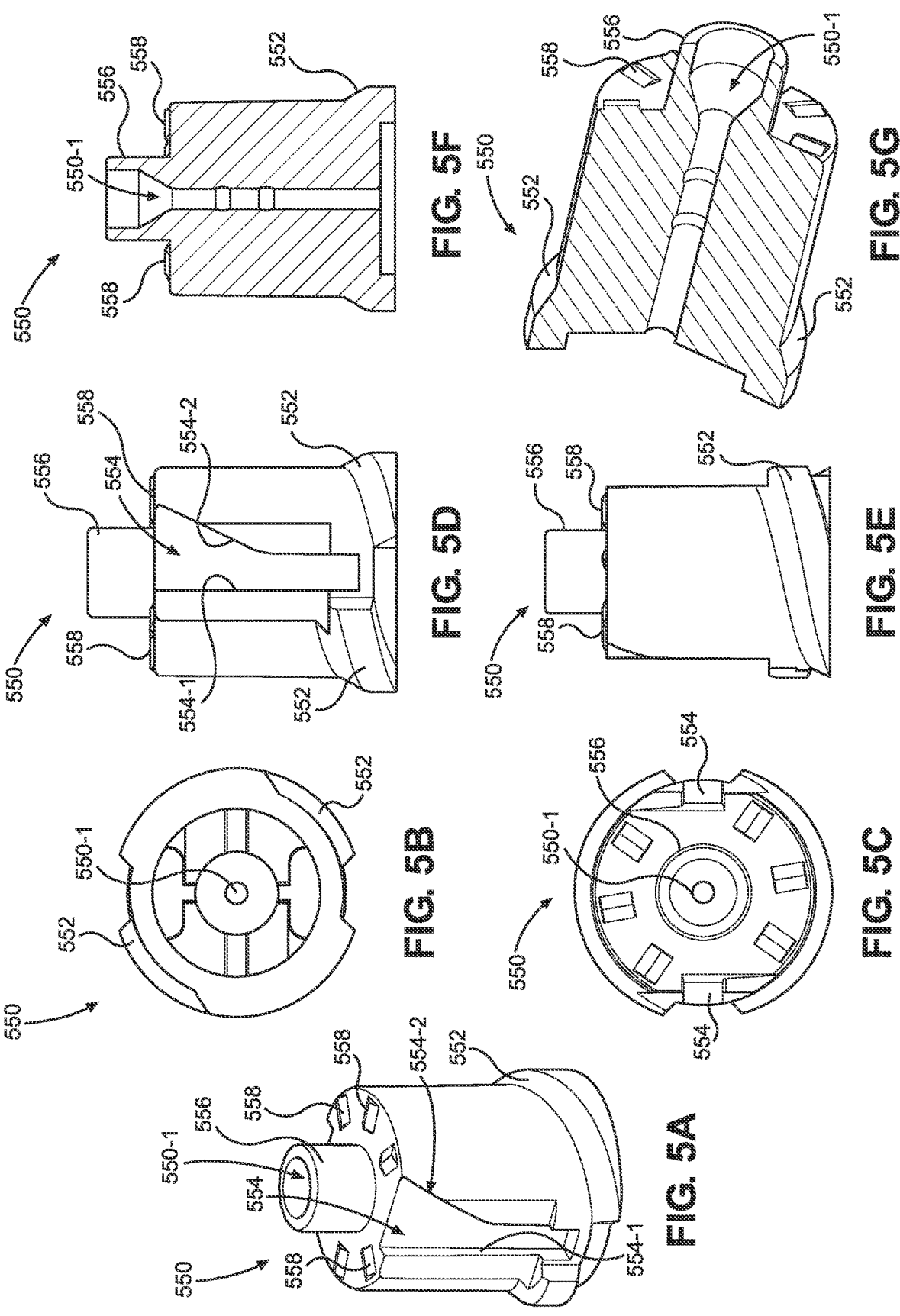
FIG. 5A, FIG. 5B, FIG. 5C, FIG. 5D, FIG. 5E, FIG. 5F, and FIG. 5G are various views of a pre-filled medical delivery assembly needle hub according to some embodiments.
Figures 6A, 6B, 6C, 6D, 6E, 6F:
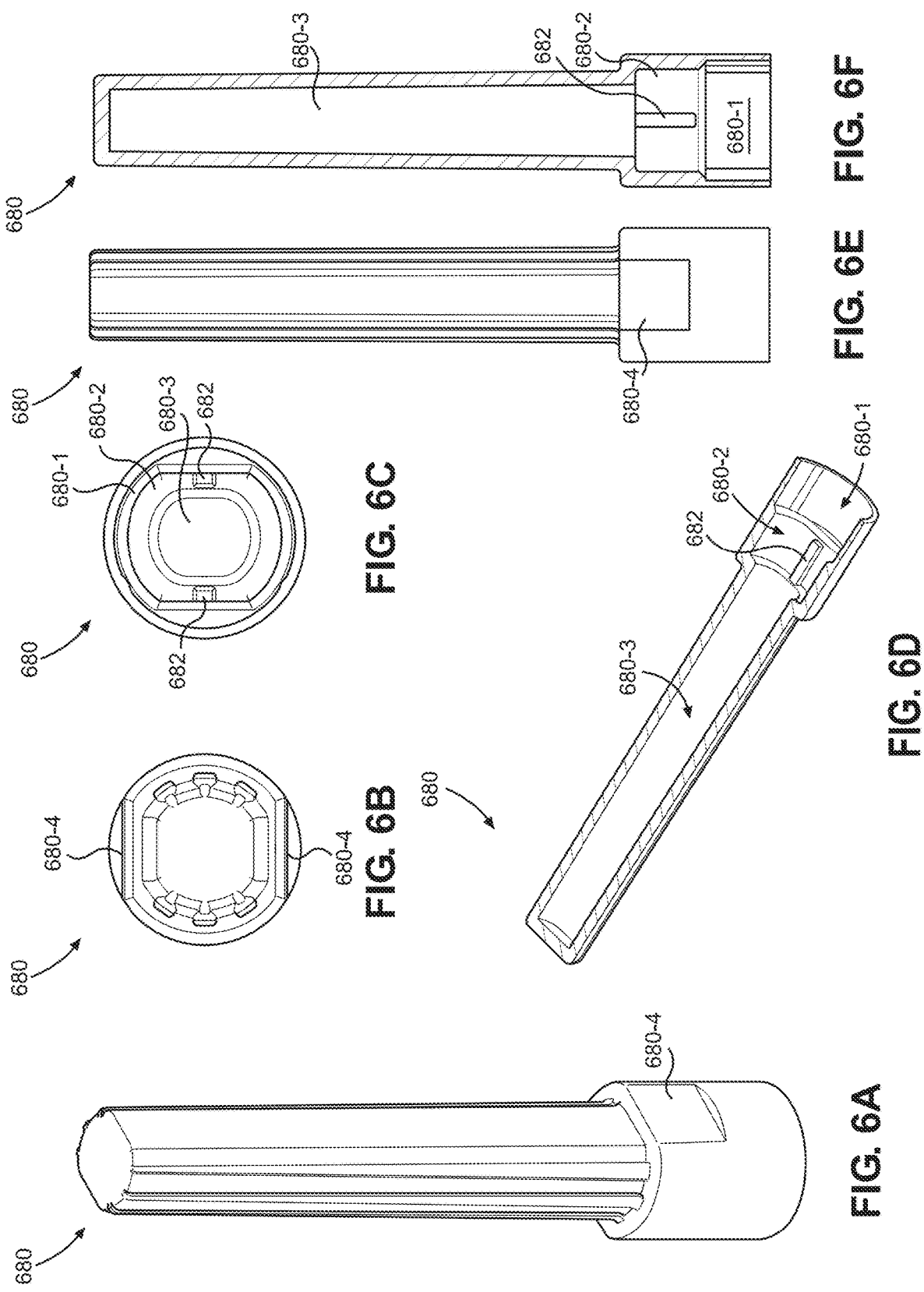
FIG. 6A, FIG. 6B, FIG. 6C, FIG. 6D, FIG. 6E, and FIG. 6F are various views of a pre-filled medical delivery assembly cap according to some embodiments.
Figures 7A, 7B, 7C, 7D, 7E, 7F:
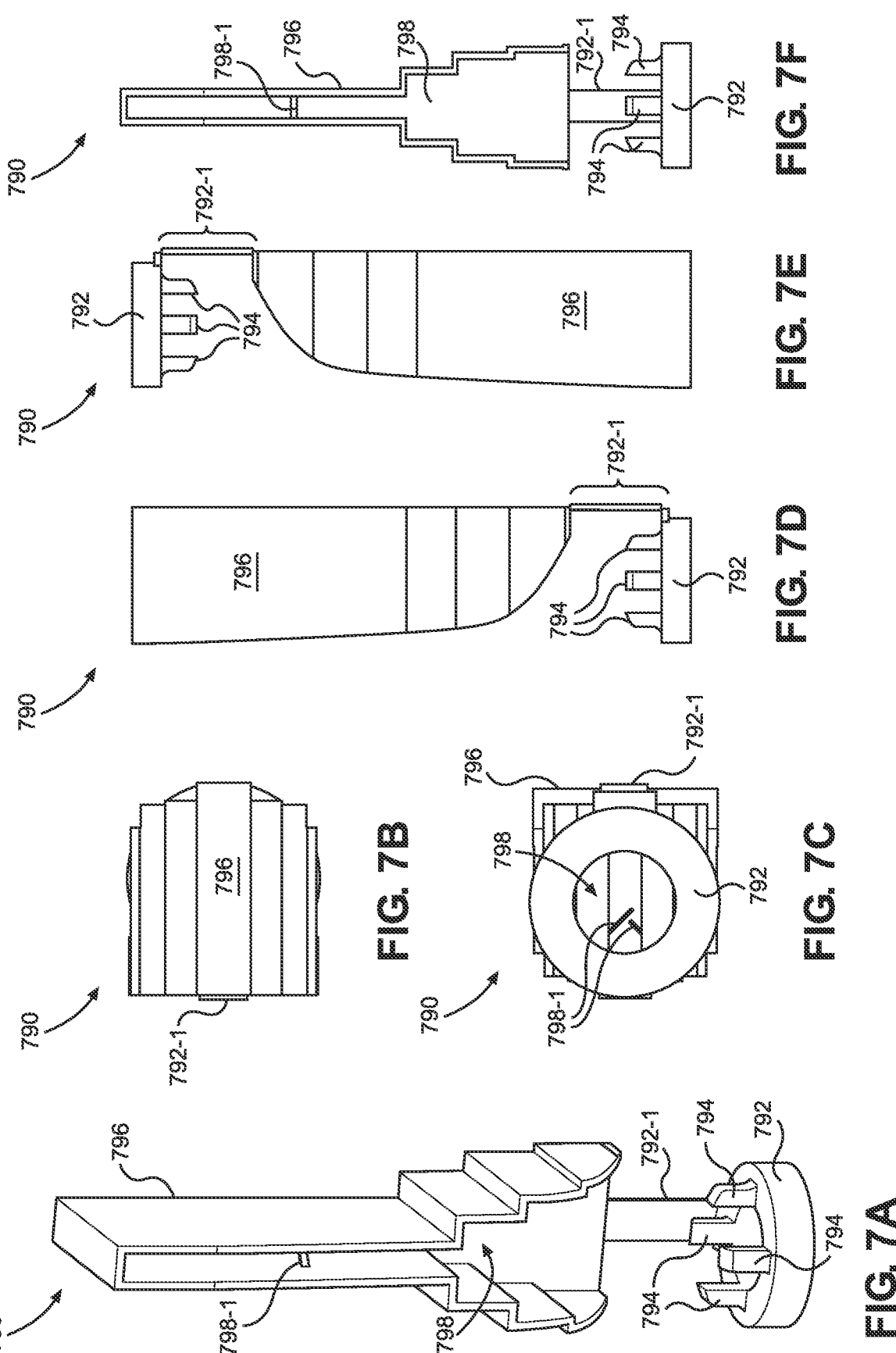
FIG. 7A, FIG. 7B, FIG. 7C, FIG. 7D, FIG. 7E, and FIG. 7F are various views of a pre-filled medical delivery assembly safety shield according to some embodiments.

In some embodiments, one or more of the mounting features 436 may be configured (e.g., sized, shaped, and/or positioned/spaced) to accept one or more corresponding mounting features of a safety shield base (not shown; such as the mounting features 394 of the safety shield base 392 of FIG. 3A, FIG. 3B, FIG. 3C, FIG. 3D, FIG. 3E, FIG. 3F, and/or FIG. 3G herein). In such a manner, for example, a safety shield (not shown; such as the safety shield 390 of FIG. 3A, FIG. 3B, FIG. 3C, FIG. 3D, FIG. 3E, FIG. 3F, and/or FIG. 3G herein) may be coupled to the coupling 432. In some embodiments, such as in the case that an attached and/or mated safety shield base comprises an opening and/or is annular in shape, the safety shield base may couple to the mounting features 436 without impeding the insertion of a BFS vial neck into the mounting socket 332-1.

According to some embodiments, fewer or more components 432-1, 432-3, 436, 438, 440, 442, 444 and/or various configurations of the depicted components 432-1, 432-3, 436, 438, 440, 442, 444 may be included in the pre-filled medical delivery assembly coupling 432 without deviating from the scope of embodiments described herein. In some embodiments, the components 432-1, 432-3, 436, 438, 440, 442, 444 may be similar in configuration and/or functionality to similarly named and/or numbered components as described herein.

Turning to FIG. 5A, FIG. 5B, FIG. 5C, FIG. 5D, FIG. 5E, FIG. 5F, and FIG. 5G, various views of a pre-filled medical delivery assembly needle hub 550 according to some embodiments are shown. The needle hub 550 (e.g., an administration member housing) may comprise similar features and/or configurations and/or may be similar to the needle hub 350 of FIG. 3A, FIG. 3B, FIG. 3C, FIG. 3D, FIG. 3E, FIG. 3F, and/or FIG. 3G herein. The needle hub 550 may comprise and/or define, for example, a hub bore 550-1, at least one external thread 552, one or more drive slots 554 (e.g., comprising and/or defining at least one drive surface 554-1 and/or at least one angled surface 554-2), a riser 556, and/or one or more projections 558. In some embodiments, the hub bore 550-1 may accept and/or house an administration member (not shown; e.g., the administration member 370 of FIG. 3A, FIG. 3B, FIG. 3C, FIG. 3D, FIG. 3E, FIG. 3F, and/or FIG. 3G herein) such as a needle. According to some embodiments, the threads 552 may be formed and/or configured to mate with corresponding threads of a BFS coupling or mating collar (not shown; e.g., the coupling 330, 430 of FIG. 3A, FIG. 3B, FIG. 3C, FIG. 3D, FIG. 3E, FIG. 3F, FIG. 3G, FIG. 4A, FIG. 4B, FIG. 4C, FIG. 4D, FIG. 4E, FIG. 4F, and/or FIG. 4G herein) such that the needle hub 550 may be securely, removably, or irremovably coupled thereto. In some embodiments, the one or more drive slots 554 (and/or the drive surfaces 554-1 thereof) may be shaped and/or configured to engage with and accept rotational force from a key (not shown) in a first rotational direction and/or to permit free rotation of the key (e.g., not engage with and/or accept rotational force from) in a second rotational direction.

According to some embodiments, the key may be disposed and/or formed on an inner surface of a cap (not shown; e.g., the cap 380 of FIG. 3A, FIG. 3B, FIG. 3C, FIG. 3D, FIG. 3E, FIG. 3F, and/or FIG. 3G herein) that is utilized as a driver to apply rotational force to the needle hub 550. The needle hub 550 may itself be disposed, for example, at least partially within a volume defined inside of the cap such that the key of the cap first into the drive slot 554. In some embodiments, the clockwise wall surface of the drive slot 554 may define the drive surface 554-1 that permits the key of the cap to advance the needle hub 550 in a clockwise (e.g., right/tight) direction. According to some embodiments, at least a portion of the counter-clockwise wall surface of the drive slot 554 may define the angled surface 554-2 that causes the key to urge axially outward from the drive slot 554 in the case that counter-clockwise (e.g., left/lose) rotation is applied. In such a manner, for example, the cap/key may be utilized to engage and/or mate the thread(s) 552 with corresponding threads (e.g., of a BFS coupling; not shown) but may not be utilized to disengage the thread(s) 552 from the corresponding threads. In some embodiments, as depicted, the thread(s) 552 may comprise a single turn of thread that traverses one hundred and eighty degrees (180°) of the circumference of the needle hub 550 or less, and/or that is bisected and/or interrupted by one or more of the drive slots 554.

In some embodiments, fewer or more components 550-1, 552, 554, 554-1, 554-2, 556, 558 and/or various configurations of the depicted components 550-1, 552, 554, 554-1, 554-2, 556, 558 may be included in the pre-filled medical delivery assembly needle hub 550 without deviating from the scope of embodiments described herein. In some embodiments, the components 550-1, 552, 554, 554-1, 554-2, 556, 558 may be similar in configuration and/or functionality to similarly named and/or numbered components as described herein.

Referring now to FIG. 6A, FIG. 6B, FIG. 6C, FIG. 6D, FIG. 6E, and FIG. 6F, various views of a pre-filled medical delivery assembly cap 680 according to some embodiments are shown. The cap 680 may comprise similar features and/or configurations and/or may be similar to the cap 380 of FIG. 3A, FIG. 3B, FIG. 3C, FIG. 3D, FIG. 3E, FIG. 3F, and/or FIG. 3G herein. The cap 680 may comprise and/or define, for example, any or all of a collar void 680-1, a needle hub void 680-2, a needle void 680-3, and/or a grip surface 680-4. In some embodiments, the collar void 680-1 may comprise an interior volume defined at a first end (e.g., an open end) of the cap 680. According to some embodiments, the collar void 680-1 may be sized and/or shaped to accept, house, and/or retain (e.g., may define a first diameter and/or first interior surface profile) at least a portion of a BFS collar and/or coupling (not shown) such as the mounting collar 332 of FIG. 3A, FIG. 3B, FIG. 3C, FIG. 3D, FIG. 3E, FIG. 3F, and/or FIG. 3G herein. In some embodiments, the needle hub void 680-2 may be formed and/or disposed adjacent to and/or contiguous with the collar void 680-1 and/or may be sized and/or shaped to accept, house, and/or retain (e.g., may define a second diameter and/or second interior surface profile) at least a portion of a needle hub (not shown) such as the needle hub 350, 450 of FIG. 3A, FIG. 3B, FIG. 3C, FIG. 3D, FIG. 3E, FIG. 3F, FIG. 3G, FIG. 4A, FIG. 4B, FIG. 4C, FIG. 4D, FIG. 4E, FIG. 4F, and/or FIG. 4G herein. According to some embodiments, the needle void 680-3 may be formed and/or disposed adjacent to and/or contiguous with the needle hub void 680-2 and/or may be sized and/or shaped to accept, house, and/or retain (e.g., may define a third diameter and/or third interior surface profile) at least a portion of a needle or other administration member (not shown) such as the administration member 370 of FIG. 3A, FIG. 3B, FIG. 3C, FIG. 3D, FIG. 3E, FIG. 3F, and/or FIG. 3G herein.

In some embodiments, the grip surface(s) 680-4 may comprise one or more planar, flat, textured, and/or parallel (e.g., in the case of two (2) or more) surfaces via which a user may grip the cap 680 to apply rotational force thereto.

According to some embodiments, such rotational force may be utilized to drive a needle hub within the needle hub void 680-2 into (or further into) a mounting collar (e.g., a BFS collar) disposed within the collar void 680-1. In some embodiments, the cap 680 and/or the needle hub void 680-2 may comprise one or more internal protrusions, features, and/or keys 682 that are operable to engage with one or more features of the needle hub. The key(s) 682 may, for example, enable a user to twist the cap 680 to impart rotational force to an engaged needle hub and/or BFS coupling attached thereto, e.g., to selectively advance an administration member (not shown) into a BFS vial (also not shown) in accordance with embodiments described herein. In such a manner, for example, the cap 680 may be utilized as a rotational driver to complete a threaded (and/or other rotational coupling) assembly of a pre-filled medical delivery assembly as described herein.

In some embodiments, fewer or more components 680-1, 680-2, 680-3, 680-4, 682 and/or various configurations of the depicted components 680-1, 680-2, 680-3, 680-4, 682 may be included in the pre-filled medical delivery assembly cap 680 without deviating from the scope of embodiments described herein. In some embodiments, the components 680-1, 680-2, 680-3, 680-4, 682 may be similar in configuration and/or functionality to similarly named and/or numbered components as described herein.

Referring now to FIG. 7A, FIG. 7B, FIG. 7C, FIG. 7D, FIG. 7E, and FIG. 7F, various views of a pre-filled medical delivery assembly safety shield 790 according to some embodiments are shown. The safety shield 790 may comprise similar features and/or configurations and/or may be similar to the cap 380 of FIG. 3A, FIG. 3B, FIG. 3C, FIG. 3D, FIG. 3E, FIG. 3F, and/or FIG. 3G herein. The safety shield 790 may comprise and/or define, for example, a shield base 792, a hinge element 792-1, one or more mounting features 794, a shield element 796 defining and/or comprising a shield space 798, and/or a needle keeper 798-1. In some embodiments, the shield base 792 may comprise a circular and/or annular ring through which a neck (not shown) of a BFS vial or bottle may pass (e.g., the neck 312 of the BFS vial 310 of FIG. 3A, FIG. 3B, FIG. 3C, FIG. 3D, FIG. 3E, FIG. 3F, and/or FIG. 3G herein). In such a manner, for example, the shield base 792 may be selectively and/or removably coupled to a BFS vial. According to some embodiments, the shield base 792 may be coupled to and/or comprise the hinge element 792-1 that may connect and/or link the shield base 792 to the shield element 796. In such a manner, for example, in the case that the shield base 792 is coupled to and/or mounted on a BFS vial, the shield element 796, by virtue of the connection via the hinge element 792-1 may also be coupled to the BFS vial. The hinge element 792-1 may comprise any type, configuration, and/or quantity of hinge and/or elastic connector between the shield base 792 and the shield element 796 that permits the shield base 792 and the shield element 796 to be selectively positioned in a plurality of different orientations with respect to each other. In the case where the hinge element 792-1 comprises a pliable and/or elastic plastic element (e.g., as shown), for example, the hinge element 792-1 may attached to the respective shield base 792 and the shield element 796 at two different points (or lines—e.g., hinge lines) and may permit repositioning about one or more of such points/lines.

In some embodiments, the shield base 792 may couple to a BFS mounting collar and/or coupling (not shown) such as the mounting collar 332 of FIG. 3A, FIG. 3B, FIG. 3C, FIG. 3D, FIG. 3E, FIG. 3F, and/or FIG. 3G herein. According to some embodiments, the one or more mounting features 794 may be sized, shaped, and/or positioned or spaced to mate with corresponding features (not shown) such as one or more of the mounting features 336 of the mounting collar 332 of FIG. 3A, FIG. 3B, FIG. 3C, FIG. 3D, FIG. 3E, FIG. 3F, and/or FIG. 3G herein. As depicted, for example, the one or more mounting features 794 may comprise axial projections that are configured to seat within corresponding axial grooves and/or seats of a mounting collar. In some embodiments, the mounting features 794 may be provided in different configurations (such as a single annular flange; not shown) or may not be utilized. According to some embodiments, the shield space 798 may be sized and/or shaped to fit over a needle (and/or other administration member; neither of which are shown; e.g., the administration member 370 of FIG. 3A, FIG. 3B, FIG. 3C, FIG. 3D, FIG. 3E, FIG. 3F, and/or FIG. 3G herein) and/or other administration component and/or module objects (also not shown). In some embodiments, the needle keeper 798-1 may be disposed in the shield space 798 to position, retain, and/or house or guide a needle/cannula, e.g., in the case that an administration member to be shielded comprises a needle and/or cannula.

In some embodiments, fewer or more components 792, 792-1, 794, 796, 798, 798-1 and/or various configurations of the depicted components 792, 792-1, 794, 796, 798, 798-1 may be included in the pre-filled medical delivery assembly safety shield 790 without deviating from the scope of embodiments described herein. In some embodiments, the components 792, 792-1, 794, 796, 798, 798-1 may be similar in configuration and/or functionality to similarly named and/or numbered components as described herein.

IV. Pre-filled Medical Delivery Methods

In some embodiments, various methods and/or processes may be performed and/or implemented to utilize a BFS vial and/or bottle filled with a single dose of medicament to administer the single dose to a patient/target. In some embodiments, a method may cause a BFS vial to be coupled to an administration component that is engaged to puncture the BFS vial and then may be utilized to inject (or otherwise administer) the medicament to the patient/target. The methods and/or processes (and/or diagrams and/or flow diagrams thereof) described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure.

In practice, for example, some or all of the following procedures may be followed to utilize a pre-filled medical delivery assembly to administer a medication (and/or other fluid) to a patient/target. In some embodiments, the area of injection may be cleaned and/or otherwise prepared. A neck and/or a fluid seal of the BFS vial (e.g., a "first" part and/or component) may be cleaned (e.g., utilizing an alcohol wipe) to prepare the BFS vial for coupling to an administration component and/or assembly. In some embodiments, a "second" part and/or component comprising a pre-packaged mounting collar/coupling, needle hub (with an administration member), cap, and/or safety shield may comprise a seal that maintains an internal volume/fluid passage in a sterile state and the seal may be removed to repaper for the coupling to the BFS vial. According to some embodiments, the administration assembly may be axially aligned with the neck of the BFS vial and the neck may be inserted into the mounting collar and/or through a base member of the safety shield to engage a mounting flange with a cooperatively shaped interior mating feature. According to some embodiments, the administration component (and/or the mounting collar and/or the safety shield thereof) may "click" or snap onto the BFS vial.

According to some embodiments, the needle hub may, as a component of a pre-packaged "second" part/administration assembly for example, be only partially engaged with (e.g., partially threaded onto) the mounting collar. Only a portion of the threads may be engaged, for example, such that the "second" part is at least loosely or partially coupled as a single object/assembly but the administration member is not advanced axially enough to pierce the BFS vial in the case that the "second" part/assembly is mated with the BFS vial. In such a manner, for example, a user may couple the "first" and "second" parts and then selectively engage the administration member to puncture the BFS vial (e.g., by application of rotational force to advance the threads/mating thereof).

In some embodiments, a user may hold the mounting collar with one hand/fingers and thread (e.g., continue threading) the needle hub fully into the mounting collar by applying rotational force to the cap. The cap may comprise an internal key that engages with the one or more stop and/or drive features of the needle hub, for example, to transfer the rotational force to the needle hub and accordingly advance the mating of the threads. As the threading/mating advances, a second or piercing end of the administration member may be axially advanced to pierce through the mounting collar (e.g., a seal portion thereof) and through the fluid seal of the BFS vial, thereby activating the pre-filled medical delivery assembly. In some embodiments, the stop/drive features may be shaped to comprise one or more surfaces that engage with the internal key of the cap in the case that the cap is rotated in a clockwise direction but may comprise an opposing surface or feature that permits (and/or forces) the internal key to disengage with the stop/drive features in the case that the cap is rotated in a counter-clockwise direction. In such a manner, for example, a user may readily couple (or complete the coupling of) the needle hub and the mounting collar but may be prevented from utilizing the cap to unscrew or decouple the needle hub and the mounting collar. In some embodiments, the internal key may be configured to accept a threshold amount of torque before a designed failure so that the user may readily tighten the threads but any attempt to overtighten will result in separation or destruction of the internal key, thereby preventing the cap from further functioning as a driver of the mating process and accordingly preventing overtightening of the mating between the needle hub and the mounting collar. In some embodiments, an audible "click" or other sound of the failure of the internal key may comprise a designed indication to the user that the pre-filled medical delivery assembly is properly and/o fully assembled/activated.

According to some embodiments, the cap may be removed to reveal the administration member and/or a first or administration end thereof. In some embodiments, the administration member (e.g., the administration end thereof) may be inserted into the patient and a collapsible reservoir of the BFS vial may be squeezed (e.g., receive an application of radially inward force), thereby expelling the fluid through the administration member and into the patient. In some embodiments, the administration member may be withdrawn from the patient and/or a safety shield (e.g., coupled to and/or part of the administration component/assembly) may be selectively moved (e.g., flipped and/or rotated) into position to cover the administration member/needle. The pre-filled medical delivery assembly may then be properly disposed of. While the mounting collar and the needle hub are generally described and depicted as separate couplable objects, in some embodiments they may be manufactured (e.g., molded) as a single object or piece or may comprise additional pieces or parts.

V. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A pre-filled medical delivery assembly, comprising:
   a blow-fill-seal (BFS) bottle defining a collapsible fluid chamber, a neck portion, and an exterior flange formed on the neck portion;
   a collar defining a first end and a second end, the first end defining a mounting socket comprising an interior seat into which the exterior flange is axially mated and the second end defining a hub socket comprising internal threads;
   a needle hub comprising at least one external thread cooperatively mated with the internal threads of the collar to a first degree of advancement, the needle hub being coupled to a double-ended needle disposed through the needle hub; and
   a cap covering an administration end of the needle and the cap comprising an interior key that is operable to drive the needle hub to advance the at least one external thread of the needle hub to a second degree of advancement with respect to the internal threads of the hub socket of the collar,
      wherein advancement of the threads to the second degree of advancement causes a piercing end of the double-ended needle to pierce a seal of the collar and to pierce a seal of the BFS bottle.

2. The pre-filled medical delivery assembly of claim 1, further comprising a safety shield coupled to the BFS bottle.

3. The pre-filled medical delivery assembly of claim 2, wherein the safety shield comprises a shield base coupled to the BFS bottle and a hinge element joining the shield base to a shield element.

4. The pre-filled medical delivery assembly of claim 1, further comprising a safety shield coupled to the collar.

5. The pre-filled medical delivery assembly of claim 1, further comprising a safety shield comprising an annular shield base through which the BFS bottle neck portion is inserted.

6. The pre-filled medical delivery assembly of claim 5, wherein the shield base comprises one or more mounting features that axially couple to corresponding features of the collar.

7. The pre-filled medical delivery assembly of claim 1, wherein the interior seat comprises an interior channel rounded at a radius in the range of four to five millimeters (4-mm to 5-mm).

8. The pre-filled medical delivery assembly of claim 1, wherein the interior seat extends radially outward into an interior wall of the mounting socket by a protrusion amount and wherein a length of the interior seat is in the range of four and three tenths times (4.3×) and five and three tenths times (5.3×) the protrusion amount.

9. A medical administration assembly, comprising:

a collar defining a first end and a second end, the first end defining a mounting socket comprising an interior seat operable to accept an exterior flange of a blow-fill-seal (BFS) bottle that is axially mated and the second end defining a hub socket comprising internal threads;

a needle hub comprising at least one external thread cooperatively mated with the internal threads of the collar to a first degree of advancement, the needle hub being coupled to a double-ended needle disposed through the needle hub; and a cap covering an administration end of the needle and the cap comprising an interior key that is operable to drive the needle hub to advance the at least one external thread of the needle hub to a second degree of advancement with respect to the internal threads of the hub socket of the collar, wherein advancement of the threads to the second degree of advancement causes a piercing end of the double-ended needle to pierce a seal of the collar.

10. The medical administration assembly of claim 9, wherein advancement of the threads to the second degree of advancement further causes the piercing end of the double-ended needle to pierce a seal of the BFS bottle.

11. The medical administration assembly of claim 9, further comprising a seal covering an opening of the mounting socket.

\* \* \* \* \*